(12) United States Patent
Vrhel et al.

(10) Patent No.: US 7,489,396 B1
(45) Date of Patent: Feb. 10, 2009

(54) SPECTROPHOTOMETRIC CAMERA

(75) Inventors: Michael J Vrhel, Sammamish, WA (US); Victor L Iseli, Everett, WA (US)

(73) Assignee: VIE Group, LLC, Sammamish, WA (US)

( * ) Notice: Subject to any disclaimer, the term of this patent is extended or adjusted under 35 U.S.C. 154(b) by 200 days.

(21) Appl. No.: 11/435,503

(22) Filed: May 17, 2006

Related U.S. Application Data

(60) Provisional application No. 60/682,304, filed on May 18, 2005, provisional application No. 60/682,305, filed on May 18, 2005.

(51) Int. Cl.
*G01J 3/42* (2006.01)
(52) U.S. Cl. .................. 356/319; 356/326; 250/226
(58) Field of Classification Search ............ 356/10, 356/300, 326, 319, 317; 250/226
See application file for complete search history.

(56) References Cited

U.S. PATENT DOCUMENTS

| | | | |
|---|---|---|---|
| 3,971,065 A | 7/1976 | Bayer | |
| 5,729,361 A | 3/1998 | Suggs | |
| 5,753,906 A | 5/1998 | Gennetten | |
| 5,859,700 A * | 1/1999 | Yang | 356/300 |
| 5,963,333 A | 10/1999 | Walowit | |
| 5,965,875 A | 10/1999 | Merrill | |
| 6,020,583 A * | 2/2000 | Walowit et al. | 250/226 |
| 6,111,244 A | 8/2000 | Wang | |
| 6,147,761 A | 11/2000 | Walowit | |
| 6,172,356 B1 | 1/2001 | Ogura | |
| 6,285,452 B1 | 9/2001 | Baker | |
| 6,295,141 B1 | 9/2001 | Ogura | |
| 6,417,508 B1 | 7/2002 | Ogura | |
| 6,847,447 B2 | 1/2005 | Ozanich | |
| 7,057,641 B2 | 6/2006 | Bodnar | |
| 7,072,034 B2 | 7/2006 | Rosengaus | |
| 7,241,262 B2 * | 7/2007 | Adler et al. | 600/130 |
| 7,295,702 B2 | 11/2007 | Vrhel | |
| 2004/0032581 A1 | 2/2004 | Nikoonahad | |
| 2005/0285129 A1 | 12/2005 | Jackson | |
| 2006/0103864 A1 | 5/2006 | Shannon | |
| 2006/0215162 A1 | 9/2006 | Shannon | |

(Continued)

OTHER PUBLICATIONS

Gunturk, B.K., et al., "Demosaicking: Color Filter Array Interpolation," *IEEE Signal Processing Magazine* 22(1):44-54, Jan. 2005.

(Continued)

*Primary Examiner*—F. L. Evans
*Assistant Examiner*—Abdullahi Nur
(74) *Attorney, Agent, or Firm*—Christensen O'Connor Johnson Kindness PLLC

(57) ABSTRACT

A spectrophotometric camera and method for measuring spectral energy in different wavelength bands at a plurality of locations are disclosed. The spectrophotometric camera comprises: a light source for sequentially producing light in different wavelength bands; an imaging device containing an array of sensors for detecting light at a plurality of locations; and a reference detector and an adjusting device for adjusting the light detected by the array of sensors. Spectral reflectance data from each of the plurality of locations on the surface of a target for each wavelength band in the plurality of light wavelength bands is measured. Spectral reflectance images are created, and features are extracted from the spectral reflectance images.

35 Claims, 12 Drawing Sheets

U.S. PATENT DOCUMENTS

2006/0215193 A1    9/2006    Shannon

OTHER PUBLICATIONS

Robertson, M.A., et al., "Dynamic Range Improvement Through Multiple Exposures," *Proceedings of the 1999 International Conference on Image Procesing (ICIP '99)*, IEEE Computer Society, Kobe, Japan, Oct. 24-28, 1999, vol. 3, pp. 159-163.

Trussell, H.J., "Applications of Set Theoretic Methods to Color Systems," *Color Research & Application* 16(1):31-41, 1991.

Unser, M., et al., "Enlargement or Reduction of Digital Images with Minimum Loss of Information," IEEE Transactions on Image Processing 4(3):247-258, Mar. 1995.

* cited by examiner

SPECTROPHOTOMETRIC CAMERA

CROSS-REFERENCE TO RELATED APPLICATION

This application claims the benefit of U.S. Provisional Patent Applications No. 60/682,304, filed May 18, 2005 and No. 60/682,305, filed May 18, 2005, the subject matter of which is also incorporated herein by reference.

BACKGROUND

Spectrometers are optical instruments used to measure electromagnetic radiation properties, e.g., light intensity, over a specific portion of the electromagnetic spectrum range from the infrared band to the gamma ray band. Normally, a particular spectrometer operates over a limited portion of this total range because different techniques are used to measure the energy in different portions of the electromagnetic spectrum. Spectrometers determine the distribution of spectral energy portions within the electromagnetic spectrum by measuring the intensity of radiation absorbed, reflected, or emitted by a material as a function of different wavelengths, separating the radiation measurements into energy bands, and indicating the relative intensities of the energy in each band. Typically, spectrometers use detectors other than photographic film to determine the distribution of radiation in a particular portion of the electromagnetic spectrum. One example of a common detector used in a spectrometer is a charge coupled device (CCD).

Spectrophotometers are spectrometers that measure the ability of a material's surface to reflect spectral energy, i.e., the spectral reflectance of the material. While the measured spectral energy is usually in the visible band of the electromagnetic spectrum, the measured spectral energy may also be in the infrared, ultraviolet, or other bands. Spectrophotometers are commonly used to measure the spectral reflectance of the surfaces of printed matter, textiles, molded and machined parts, etc., for quality control and/or process characterization. A spectrophotometer typically measures integrated spectral reflectance in a small circular area, e.g., an area four to eight millimeters in diameter, thereby providing only one number to represent what may in reality be spectral energy at a plurality of different wavelengths, each of which varies in intensity at different locations within the circular area. Even though four to eight millimeters is a relatively small area, for many surfaces, e.g., textiles, spectral reflectance can vary widely over a surface area of this size. Hence, it is difficult to use a single spectrophotometer measurement to precisely determine how reflected spectral energy varies over a particular surface area.

One way to measure reflected spectral energy whose intensity in different bands varies over a surface is to take multiple, simultaneous samples across a grid of locations on the surface. Preferably, the spacing of the locations in the grid is small enough to provide information about the spatial variation of the surface's spectral reflectance. One way to take multiple, simultaneous, closely spaced samples over a surface is to use a digital camera. Typically, in a digital camera, radiant energy, e.g., light, passes through a lens, an aperture, a color filter array and strikes a two dimensional sensor array that records the radiant energy. The sensors in digital camera sensor arrays are often charge coupled devices (CCDs). A CCD is an integrated circuit containing an array of light-sensitive diodes that convert radiant energy into an electrical charge proportional to the intensity of the radiant energy. Each diode has a capacitor that can accumulate charge over an exposure time. Circuitry external to the CCD array converts the charge in each CCD element to a voltage that is converted to a digital value that is stored in an electronic memory device. Used conventionally, the array of values from the CCD array are viewed as an image with each CCD providing one picture element (pixel) in the image. An alternative to a CCD array is an Active Pixel Sensor (APS). An APS is a complementary metal oxide semiconductor (CMOS) device in which the sensing circuitry is combined with the recording circuitry.

SUMMARY

A spectrometric system suitable for implementation as a spectrophotometric camera and a method for measuring spectral energy in different wavelength bands at a plurality of locations is disclosed. In one exemplary form, the spectrometric system comprises a spectral energy source capable of sequentially producing spectral energy in different wavelength bands; an imaging device containing an array of sensors for detecting spectral energy at a plurality of locations; a first spectral director for directing the spectral energy produced by the spectral energy source onto a target surface; a second spectral director for directing spectral energy reflected from the target surface to the imaging device array of sensors; a reference detector for sensing changes in the spectral energy from the spectral energy source; and an adjusting device for adjusting the spectral energy detected by the sensors of the array of sensors according to the changes sensed by the reference detector.

Depending on implementation, the spectral energy wavelength bands produced and detected by the spectrometric system are in one or more of the ultraviolet, visible, and infrared regions of the electromagnetic spectrum.

An exemplary spectrophotometric camera comprises: a light source for sequentially producing light in different wavelength bands; an imaging device containing an array of sensors for detecting light at a plurality of locations; a first light pipe for directing the light sequentially produced by said light source onto a target surface; a second light pipe for directing light reflected from the target surface to the imaging device array of sensors; a reference detector for sensing changes in the light of each wavelength band produced by the light source; and an adjusting device for adjusting the light detected by the sensors of the array of sensors according to changes sensed by the reference detector.

The method collects spectral energy data in a plurality of light wavelength bands reflected from a plurality of locations on a surface. The spectral energy data reflected from each of the plurality of locations on the surface for each wavelength band in the plurality of light wavelength bands is collected in spectral reflectance data images. The spectral reflectance data images are error corrected and analyzed. If multiple spectral reflectance data images are collected for each wavelength band, the collected images for each wavelength band are merged prior to analysis.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
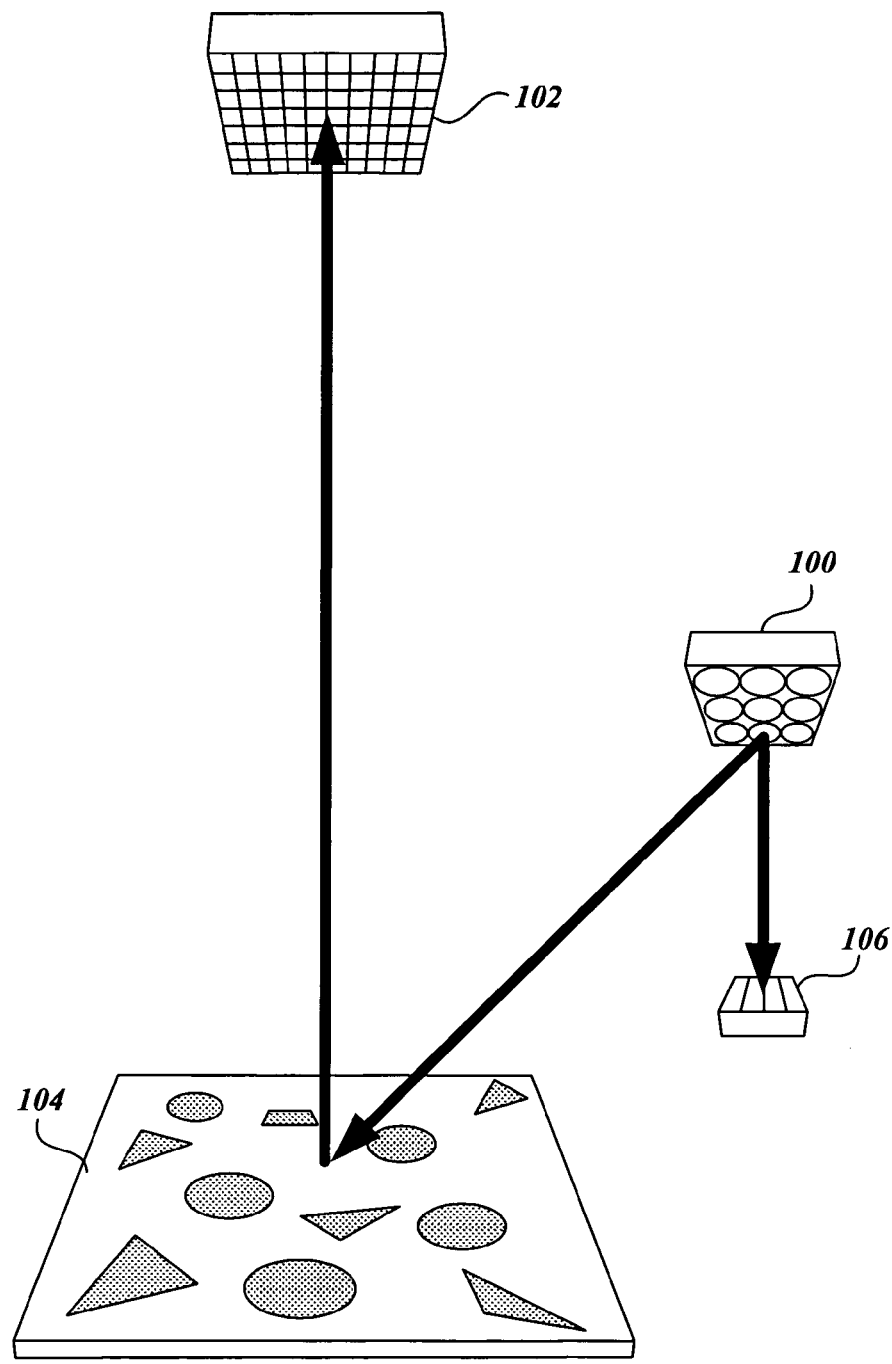
FIG. 1 is a pictorial illustration of selected elements of a model of an exemplary system that provides spectral reflectance data.

The spectral energy reflected from a surface ("spectral reflectance"), such as the surface of printed matter, textile, molded or machined part, etc., often varies in intensity and/or wavelength from one location to another across the surface. The distances between locations may be small, e.g., less than a millimeter. Typical spectrophotometers provide one integrated measurement of a surface area with a diameter of roughly 4 mm to 24 mm. Such integrated measurements are described by the following equation:

$$m(\lambda) = \int_{(x,y) \in A} r(\lambda,x,y) dx dy \; \lambda = 400, 410, \ldots, 690, 700 \text{ nm} \quad (1)$$

In equation (1) $m(\lambda)$ is a spectrophotometer measurement for wavelength $\lambda$; A is the spectrophotometer aperture size; and $r(\lambda,x,y)$ is the spectral reflectance of the surface at spatial location x and y for wavelength $\lambda$. Spectrophotometer measurements are unable to distinguish variations in surface spectral reflectance intensity that are less than about 4 mm apart. In addition, in a single capture, traditional spectrophotometers provide the spectral reflectance at only one integrated spatial location of the sample surface. In many applications, it is desired to capture spectral reflectance information at high spatial resolution across a large surface.

In contrast, digital cameras are able to distinguish variations in surface spectral reflectance intensity that are less than 4 mm apart. In addition, digital cameras provide measurements at multiple spatial locations in a single capture. Typically, color digital cameras provide measurements for three wavelength bands: red, green, and blue. Such measurements are modeled by the following equation:

$$s_i(x,y) = \int \int r(\lambda,x,y) l(\lambda,x,y) f_i(\lambda) d\lambda dt \quad i=1,2,3 \quad (2)$$

In equation (2), $s_i(x,y)$ $i=1, 2, 3$ are the three wavelength band spectral measurements; $r(\lambda,x,y)$ is the spectral reflectance of the surface at spatial location x and y for wavelength $\lambda$; $l(\lambda,x,y)$ is the illumination spectrum at the spatial locations x and y for wavelength $\lambda$ and $f_i(\lambda)$ $i=1, 2, 3$ is the spectral sensitivity of the three wavelength bands. The integration is performed over time and wavelength $\lambda$.

The integration described by equation (2) is performed for each pixel in the CCD array of a color digital camera. Since each pixel covers an area that is significantly smaller than the 4 mm diameter area covered by a spectrophotometer, color digital cameras are able to distinguish variations in spectral reflectance intensity that are less than 4 mm apart. In addition, color digital cameras each contain an array of sensors and are thus able to record measurements at multiple locations in a single capture. While color digital cameras are able to distinguish spectral reflectance variations over small areas, with no other processing, the three wavelength bands available in color digital cameras limit their spectral resolution. Hence, color digital cameras are rarely sufficient to quantify the spectral characteristics of a surface. The spectrometric system described herein combines the spectral range and spectral resolution of a spectrophotometer with the spatial range and spatial resolution of a digital camera. The spectrometric system provides measurements of $r(\lambda,x,y)$ on a spatial grid and at specific wavelengths. Illuminating a surface with spectral energy lying within a narrow wavelength band allows the spectrometric system to record the spectral reflectance lying within the narrow wavelength band at a plurality of locations on the surface. More specifically, the spectrometric system records data by forming an image of the reflected spectral energy lying within the narrow wavelength band for each of the plurality of locations. Illuminating the surface with different wavelength bands allows one or more spectral energy data images to be created for each wavelength band.

The output of a spectrometric system, such as a spectrophotometric camera, is typically a spectral energy data image. A spectral energy data image that is produced by a spectrometric system may be viewed on the display of a computing device. A spectral energy data image may also be used as input data for computerized devices used in automated processes. For example, a spectral energy data image produced by a spectrometric system may be input into the controls of a computerized printing press to adjust the flow of an ink applied by the printing press to increase or decrease the density of a printed image.

FIG. 1 is a pictorial illustration of a model of an exemplary spectrometric system that produces spectral reflectance data for each wavelength band of a plurality of wavelength bands of spectral energy reflected from a plurality of locations on a surface. For ease of illustration and understanding, only light emitting and detecting components are illustrated in FIG. 1. Optical and other components of the spectrometric system are not included in the model illustrated in FIG. 1. The model illustrated in FIG. 1 includes a spectral energy source, i.e., a light source 100, that produces spectral energy in a plurality of wavelength bands in a serially selectable fashion. Spectral energy, i.e., light in a particular wavelength band produced by the light source 100, is directed onto a target surface 104.

A portion, i.e., a percentage, of the light that strikes the target surface 104 is reflected. The target surface's reflected light is directed to a multiple pixel sensor array 102, such as the CCD array of a digital camera. As noted above, the light source 100 produces light in a plurality of wavelength bands in a serially selectable fashion. This is accomplished by the light source 100 including an array of light emitting diodes (LEDs) each emitting a different wavelength band and connected to a control that enables each LED to be individually turned on and off. The number of LEDs turned on and off, of course, relates to the number of wavelength bands whose effect is to be recorded by the multiple pixel sensor array 102 and the reference detector 106. Turning on one LED at a time while maintaining the remaining LEDs off results in light in one wavelength band being produced.

Figure 3:
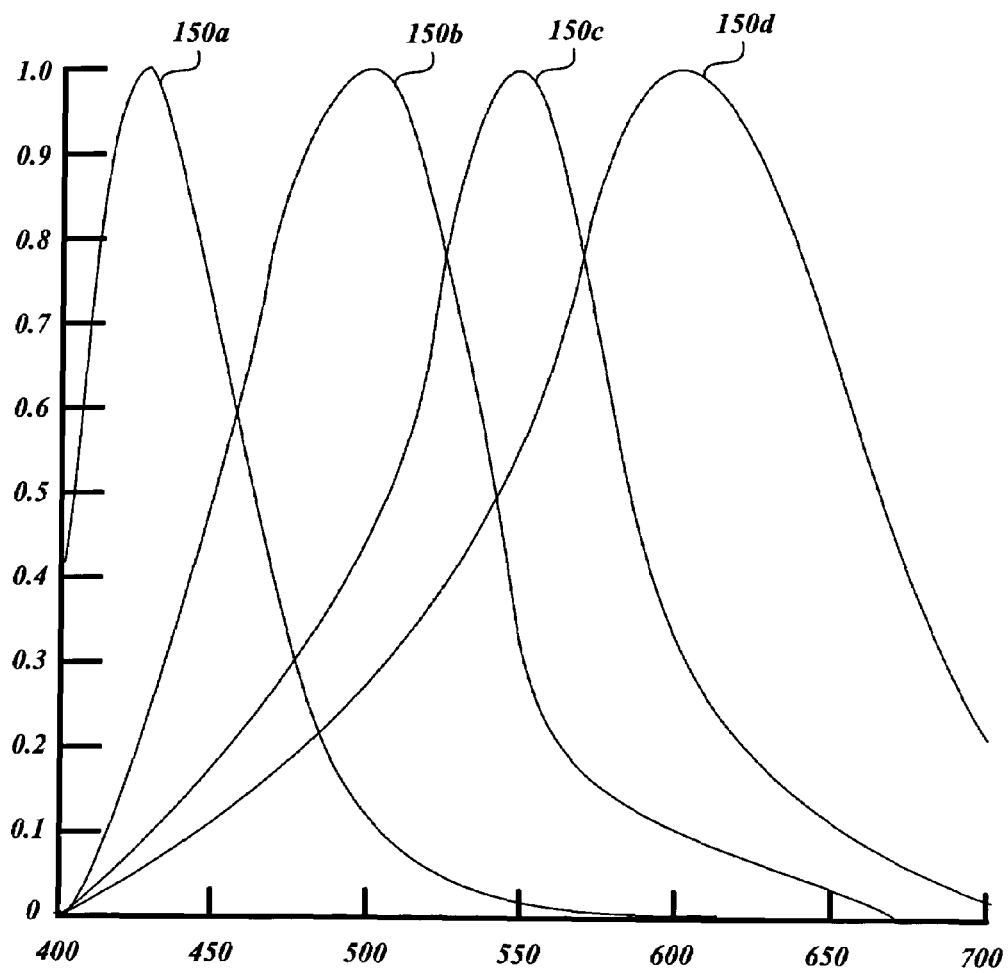
FIG. 3 is a chart illustrating the energy distribution of the wavelengths of visible light emanating from four exemplary light sources, e.g., four light-emitting diodes.

As illustrated in FIG. 3 and described below, each wavelength band covers a predetermined portion of the electromagnetic spectrum. The light that strikes the target surface 104 and the reference detector 106 lies within the wavelength band of the turned on LED. The light that strikes the target surface 104 is reflected from multiple locations on the target surface. As noted above, a portion of the reflected light strikes the multiple pixel sensor array 102, which records an image of the light reflected from multiple locations over an image area of the target surface 104. As a result, a spectral image of the reflected light lying in the wavelength band of the turned on LED is obtained.

Figure 6:
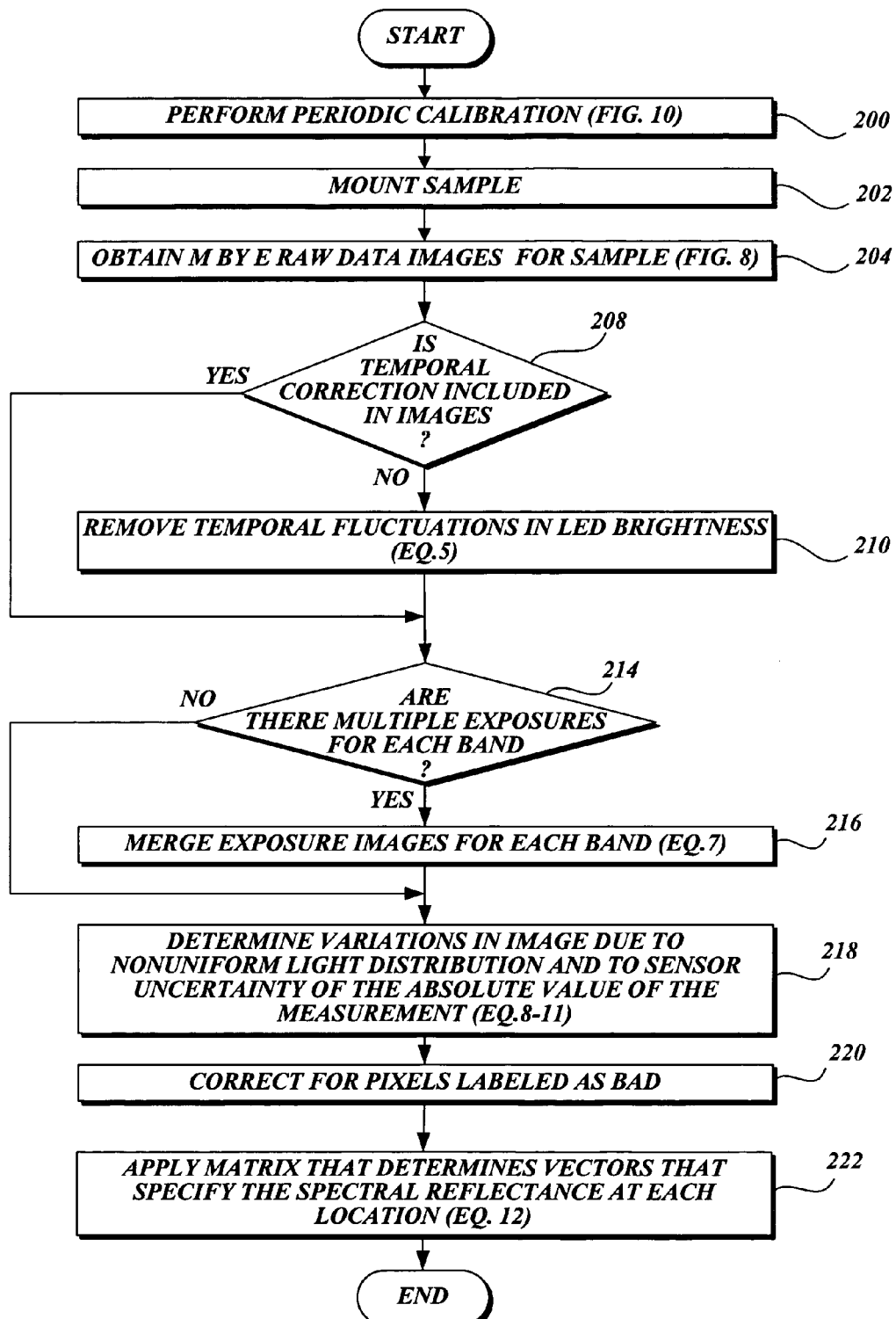
FIG. 6 is a flow diagram illustrating an exemplary method for collecting spectral reflectance data from a plurality of locations on a surface.

The characteristics of the light produced by a physical light source such as an LED change over time. The reference detector 106 detects such changes. More specifically, the reference detector 106 detects changes in the intensity of the light produced by each LED in the wavelength band produced by the LED over time. The changes in the light intensity of each LED detected by the reference detector 106 are used to adjust the spectral image data recorded by the multiple pixel sensor array 102. The preferred method of performing this adjustment is illustrated in FIG. 6 and described below. An exemplary spectrophotometric system for controlling the operation of the elements of the exemplary model illustrated in FIG. 1 is illustrated in block diagram form in FIG. 2.

Figure 2:
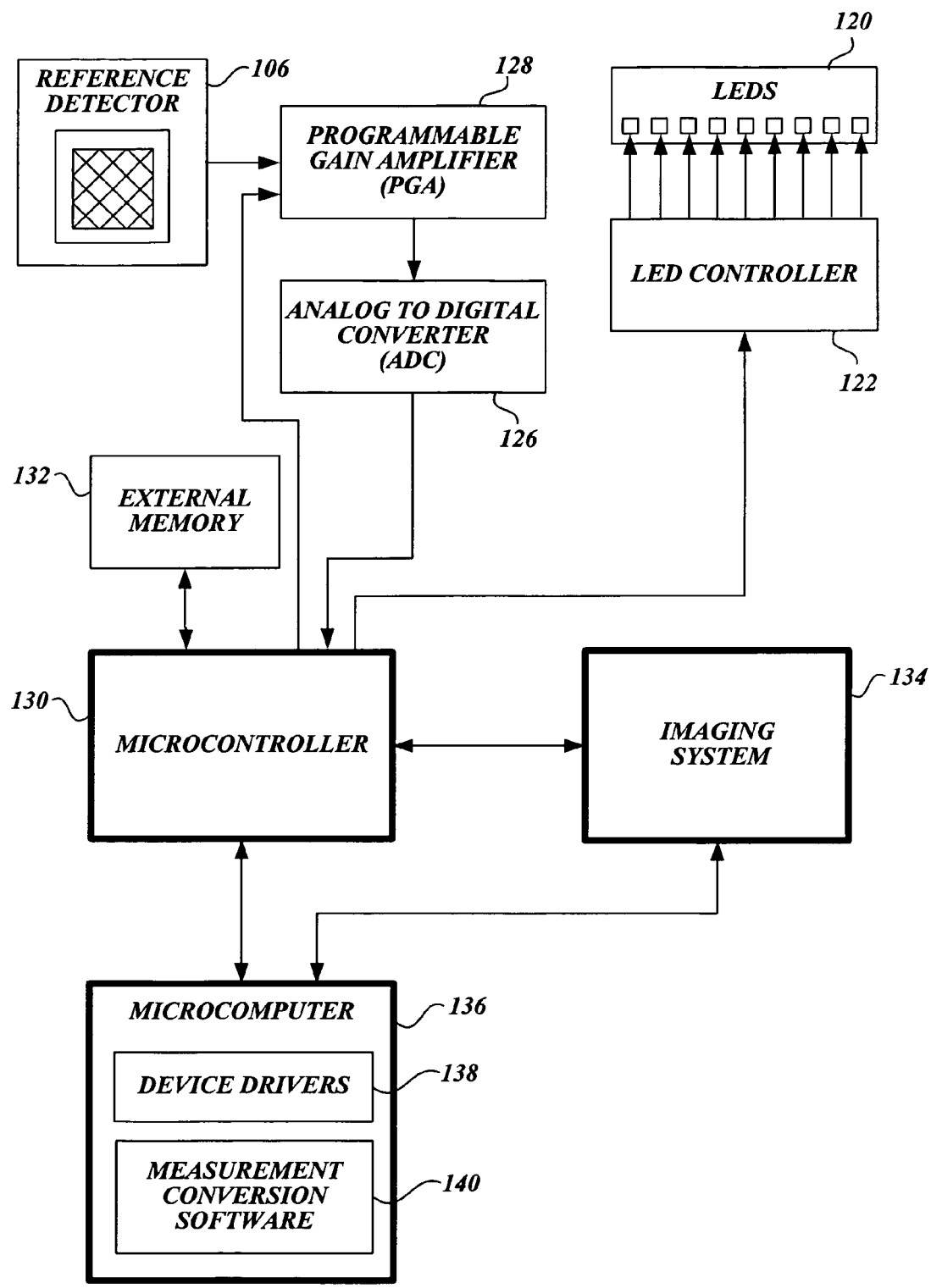
FIG. 2 is a block diagram of an exemplary spectrophotometric system that collects and analyzes spectral reflectance data.

FIG. 2 includes an LED array 120 that performs the function of the light source 100 shown in FIG. 1. An LED controller 122 controls the operation of the LED array 120. The LED controller 122 sequentially turns each LED of the LED array 120 on while maintaining the other LEDs off, as directed by a microcontroller 130 connected to the LED controller 122. Depending on implementation details, the microcontroller can be in any one of a variety of forms—a field programmable gate array (FPGA) or an application specific integrated circuit (ASIC), for example. The microcontroller 130 is connected to and controlled by a microcomputer 136 that contains device drivers 138 and measurement conversion software 140.

The microcontroller 130 is also connected to an imaging system 134 that includes the multiple pixel sensor array 102, shown in FIG. 1. More specifically, in addition to a multiple pixel sensor array, the imaging sensing system includes other elements and components, such as optical components, electrical interface components, etc. An external memory 132 is connected to the microcontroller 130 for storing data, such as the data collected by the imaging system 134.

The microcontroller 130 is also connected to the control input of a programmable gain amplifier (PGA) 128. The signal input of the PGA is connected to the output of the reference detector 106. As described above, the reference detector 106 detects changes in the illumination produced by the LED array 120. The PGA is used to adjust the gain of signals generated by the reference detector 106. The adjusted signals are applied to an analog to digital converter (ADC) 126 that converts the adjusted analog signals produced by the reference detector 106 into digital data signals. The digital data signals produced by the ADC 126 are sent to the microcontroller 130.

The microcomputer 136 may include hardware and software components in addition to the device drivers 138 and measurement conversion software 140. Instructions that direct the microcontroller 132 and imaging system 134 may be stored in the device drivers 138 and/or the measurement conversion software 140 and/or in another software component that controls the operation of the microcomputer 136. The measurement conversion software 140 includes software for adjusting the magnitude of the spectral energy detected by the sensor array of the imaging system 134 based on changes in the spectral energy detected by the reference detector 106. The measurement conversion software 140 also includes software for compensating for less than ideal spectral distribution of the LED sources. Preferably, the imaging system 134 is sensitive across the entire visible region of the electromagnetic spectrum. As noted above, the three wavelength bands available in color digital cameras restrict the ability of color digital cameras to provide sufficient spectral resolution across the entire visible region of the electromagnetic spectrum to quantify the spectral characteristics of a surface. In order to provide sufficient spectral resolution, preferably the imaging system 134 does not include color separation because color separation might limit the imaging system sensitivity. Instead, preferably, the imaging system 134 is a monochrome digital camera having sensitivity across the entire visible spectrum. The wavelength differentiation provided in a color digital camera by RGB color filters is provided in the herein described spectrophotometric system by sequentially activating LEDs that each produce light in a narrow wavelength band. Also preferably, the imaging system 134 has an infrared (IR) filter to block IR, and has a blocking aperture and enclosure to protect the multiple pixel sensor array in the imaging system from unwanted light. Further, preferably, the imaging system 134 is able to control exposure time and amplifier gain to enable the capturing of multiple exposures of an image to thereby significantly increase the dynamic range of the overall image data. As noted above, a monochrome digital camera is an example of a suitable imaging system 134.

If desired, computing devices such as, but not limited to, desktop or laptop computers, programmable calculators, etc., may be used in place of the microcomputer 136. Hence, the use of microcomputer 136 to control the microcontroller 130 and the imaging system 134 should be construed as exemplary and not limiting. Likewise regarding the microcontroller and other components illustrated in FIG. 2. The herein described functions of these components may be performed by other components or integrated with other components.

In the illustrated exemplary embodiment, instructions produced by the microcomputer 136 cause the microcontroller 130 to control the LED controller 122 such that, as described above, the LEDs of the LED array 120 are turned on or off in a predetermined order and such that when one LED in the LED array 120 is turned on, the remaining LEDs in the LED array 120 are turned off. The energized LED produces light in a wavelength band. The spectral energy of the light is distributed across the wavelengths of the wavelength band and may be represented by a wavelength band distribution curve. A few (four) examples of wavelength band distribution curves are shown in FIG. 3.

FIG. 3 is a chart that includes four spectral energy distribution curves 150a, 150b, 150c, and 150d covering four exemplary wavelength bands. Each exemplary wavelength band represents the spectral energy produced by a single LED. As will be readily understood by those skilled in the art and others, most actual embodiments of the invention will include substantially more than four LEDs. For ease of illustration and understanding, FIG. 3 depicts only four spectral energy curves. In an actual embodiment of the invention, the number of LEDs and thus the number of curves would be such that the spectral energy above a predetermined magnitude would be produced across the entire range of interest. Thus, a larger number of actual spectral energy curves 150a, 150b, 150c, 150d . . . 150n would actually exist.

The horizontal axis of the chart shown in FIG. 3 is divided into wavelengths of the visible spectrum, i.e., 400 to 700 nanometers, in 50-nanometer increments. The chart's vertical axis is divided into relative energy distribution percentages ranging from 0 to 100% in 10 percent increments. The exemplary spectral energy distribution curves 150a, 150b, 150c, and 150d bound the spectral energy distribution for wavelengths within a particular wavelength band. For example, the wavelengths contained by the spectral energy distribution curve 150a range from roughly 400 nanometers to roughly 600 nanometers in length. The amount over a predetermined percentage, e.g., 90% of the total spectral energy for this curve, ranges from about 420 nanometers to about 440 nanometers. Adding additional LEDs with appropriate wavelength bands would allow 90% of the total spectral energy to be produced by "on" LEDs over the entire desired, e.g., visible, spectrum range.

As shown in FIG. 1 and described above, light from an LED in light source 100, i.e., the switched on LED of the LED array 120 (FIG. 2), is directed to the reference detector 106. The amplification of the analog signal produced as a result of the light detected by the reference detector 106 is controlled by the PGA 128. As noted above, the amplified analog signal is converted to a digital signal by the ADC 126. As also noted above, the ADC 126 transmits the digital data signal to the microcontroller 130, which forwards the digital data to the microcomputer 136. The measurement conversion software 140, in turn, processes the digital data.

In a somewhat similar fashion, as also shown in FIG. 1, light from an LED in light source 100, i.e., the switched on LED of the LED array 120 (FIG. 2), is also directed to the target surface 104. The light reflected from the target surface 104 is directed to the imaging system 134. The sensor array of the imaging system 134, as shown in FIG. 1 and described above, includes a multiple pixel sensor array 102. As previously described, the multiple pixel sensor array 102 records a spectral energy image of the spectral energy of the light reflected from a target surface area. The spectral energy image is transmitted to the microcontroller 130 for storage in memory, such as the external memory 132 or directly to the microcomputer. As described more fully below, the measurement conversion software 140 of the microcomputer 136 uses the digital data from the reference detector 106 to adjust the spectral energy image, i.e., the spectral image, stored in memory.

The spectral image that is recorded by the multiple pixel sensor array 102 and stored in memory comprises an array of picture elements (pixels), i.e., a pixel array. Each pixel in the pixel array records a measurement of the spectral energy reflected from a specific location on a target surface. At least one spectral image is recorded for each wavelength band produced by the light source 100. The result is a set of spectral images.

Figure 4:
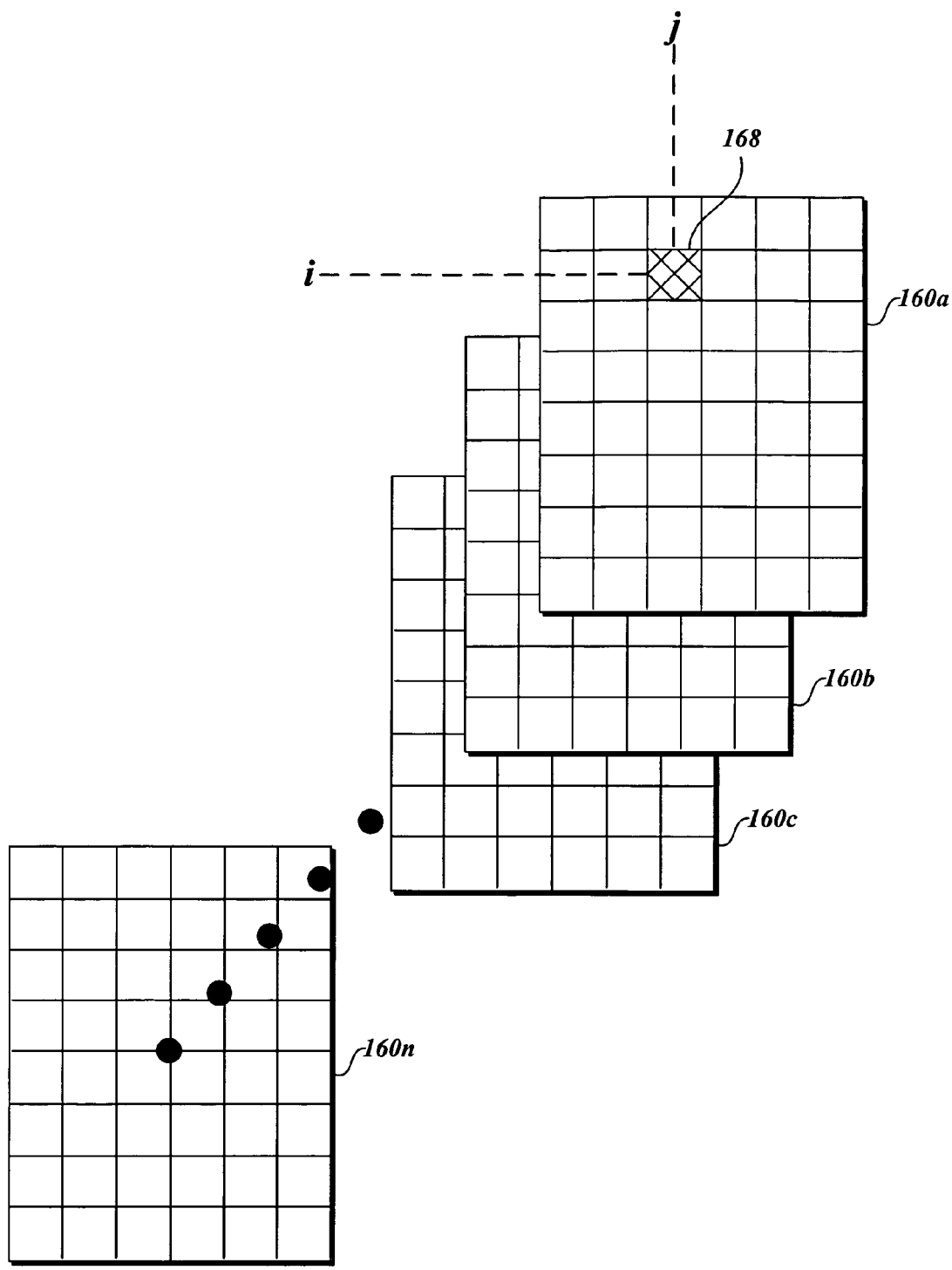
FIG. 4 is an illustration of an exemplary pixel at an exemplary location in one of a plurality of exemplary spectral reflectance images derived from an exemplary surface.

FIG. 4 is an illustration of an exemplary set of exemplary spectral images 160a, 160b, 160c . . . 160n that, for example, may be produced by recording spectral images for wavelength bands represented by the spectral energy distribution curves in FIG. 3. In particular, a wavelength band produced by an LED of the LED array 120 is represented by one of the spectral energy distribution curves shown in FIG. 3, e.g., the spectral energy distribution curve 150a. The spectral energy in the wavelength band produced by the LED of the LED array 120 and represented by the spectral energy distribution curve 150a is recorded as a spectral image, e.g., the spectral image 160a. Similarly, the spectral energy in a second exemplary wavelength band produced by a second exemplary LED of the LED array 120, represented by the spectral energy distribution curve 150b, is recorded as the spectral image 160b; the spectral energy in a third exemplary wavelength band produced by a third exemplary LED of the LED array 120, represented by the spectral energy distribution curve 150c, is recorded as the spectral image 160c; and so on for each of the LEDs in the LED array 120. In this way, a set of spectral images is produced comprising one spectral image for the spectral energy for each of the wavelength bands sequentially produced by the LED array 120. Each pixel in each spectral image records a measurement of the spectral energy of a specific wavelength band that is reflected from a specific location on the target surface 104.

Those skilled in the art will appreciate that the number of pixels in a spectral image produced by the imaging system 134 is substantially greater than the number of pixels shown in the exemplary spectral images 160a, 160b, 160c . . . 160n illustrated in FIG. 4 and that the size of each pixel is much smaller than the pixels shown in FIG. 4. In order to more clearly illustrate individual pixels, a relatively small quantity of pixels in each spectral image is shown in FIG. 4 and the pixels that are shown are much larger than physical pixels in an actual spectral image.

In the example described above, each exemplary spectral image in the exemplary set of spectral images shown in FIG. 4 is produced by activating one LED of the LED array 120 to produce a wavelength band, such as a wavelength band represented by the spectral energy distribution curve 150a; directing the spectral energy produced by the activated LED to a target surface, such as target surface 104; directing the spectral energy reflected by the target surface 104 to a multiple pixel sensor array, such as multiple pixel sensor array 102; and recording the spectral image captured by the multiple pixel sensor array such as spectral image 160a. Each pixel in a spectral image has a value that represents the spectral energy reflected from the target surface 104 at a particular location on the target surface 104. For example, as shown in FIG. 4, a pixel at i,j coordinates 3, 2 may record a spectral energy value, of, for example, 400 units of spectral energy, reflected from the target surface 104 at related coordinates of the target surface 104.

Preferably, one spectral image is produced for each wavelength band. More specifically, if the imaging system 134 is of sufficient quality, adequate results may be achieved by producing one spectral image for each wavelength band. If the imaging system is of lower quality, e.g., less sophisticated and/or less expensive, the imaging system may be unable to produce spectral images of sufficient quality. To compensate for this lack of quality, a plurality of raw data images for each wavelength band may be obtained and the plurality merged into one spectral image.

In a spectrometric system, such as the spectrometric system modeled in FIG. 1 and described above, the angle at which the spectral energy strikes a surface and the angle at which the spectral energy that is reflected from the surface and enters a detector, such as the multiple pixel sensor array 102, affects the quality of the spectral images that are produced as well as the type of information about the sample that is recorded. In order to produce spectral images of consistent quality, preferably, the spectral energy is directed such that the spectral energy strikes the target surface 104 at a 45 degree angle and the reflected spectral energy enters the detector, i.e., the multiple pixel sensor array 102, at a zero degree angle. Those skilled in the art often refer to a geometrical relationship in which spectral energy light, strikes a surface at a 45 degree angle and enters a detector at a 0 degree angle as a 45-0 geometry. Note that other optical geometries are possible if other information (e.g. glossiness) about the sample surface 104 is desired.

Figure 5:
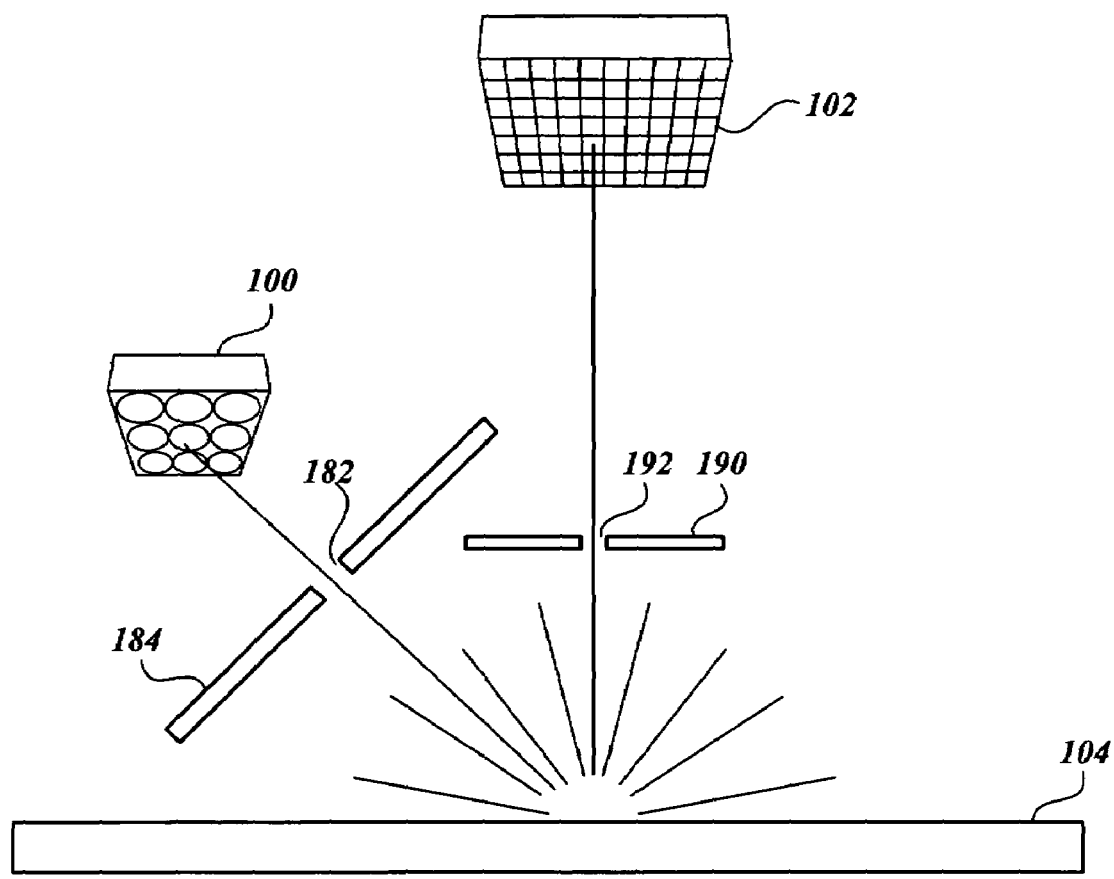
FIG. 5 is an exemplary illustration of using an aperture to direct light onto a surface at a 45 degree angle and using an aperture to direct light reflected from the surface at a 0 degree angle to an array of sensors.

FIG. 5 is a schematic illustration of an exemplary 45-0 geometry. The images are symbolic and the sizes and distances in FIG. 5 are not to scale. In FIG. 5, spectral energy, i.e., light, from the light source 100 travels through an aperture 182 in an aperture plate 184. To insure that the light is directed at 45 degree angle to the target surface 104, the aperture plate 184 is angled at 45 degrees to the target surface 104. Those skilled in the art will appreciate that the aperture plate 184 may be used to control the amount of light directed to the target surface 104 as well as the angle at which the light strikes the target surface 104. Typically the aperture 182 does not affect or control the wavelength or wavelengths of the light. The aperture 182 may however contain a color filter to better control the spectral power distribution of the light source 100. Typically, light striking the target surface 104 at 45 degrees is reflected at a plurality of angles. To insure that the light reflected from the target surface 104 enters the detector, i.e., the multiple pixel sensor array 102, at a 0 degree angle, an aperture plate 190 having aperture 192, lying parallel to the target surface 104, is positioned between the target surface 104 and multiple pixel sensor array 102. Since many configurations of light sources, apertures, surfaces, and detectors are possible and there are many ways to achieve a 45-0 geometry, the geometrical positioning illustrated in FIG. 5 and described above should be construed as exemplary and not limiting. For example, the apertures may incorporate lenses to provide for more control and an improved system signal-to-noise ratio.

In summary, the exemplary spectrophotometric system illustrated in block diagram form in FIG. 2 and described above, includes the components of a spectrometric system such as the spectrometric system shown in FIG. 1, namely, a serially selectable spectral energy source, e.g., light source 100; a spectral image recording device, e.g., multiple pixel sensor array 102; a target surface, e.g., target surface 104; and a reference detector, e.g., reference detector 106. Preferably, the spectrophotometric system has a 45-0 geometry, an example of which is shown in FIG. 5. As noted above, the exemplary spectrophotometric system illustrated in FIG. 2 is used to measure spectral reflectance for a plurality of wavelength bands at a plurality of locations on a target surface.

The flow diagram shown in FIG. 6 illustrates an exemplary method suitable for controlling the operation of the exemplary spectrophotometric system illustrated in FIG. 2. As described more fully below, the method controls the collection of a number of raw spectral reflectance images using a sensor array, such as the multiple pixel sensor array 102. The raw spectral reflectance images are converted into a number of useable spectral reflectance data images. The resulting spectral reflectance data images contain spectral reflectance data for a number of wavelength bands, preferably each of a uniform size, e.g., 10 nanometers, within a region of the electromagnetic spectrum. Ideally, the entire visible spectrum from about 400 to 700 nm is uniformly sampled.

The method illustrated in FIG. 6 begins at block 200 where periodic calibration is performed. Periodic calibration serves three purposes. A first purpose of periodic calibration is to compensate for nonuniform illumination across a sample. For example, a particular LED may shine more light on one location of the sample surface 104 compared to another location of the sample surface 104. It is desirable to remove the variation of illumination between locations from the recorded data. A second purpose of periodic calibration is to enable the system to produce data that accurately describes a standard reflectance sample surface. That is, if a known standard reflectance sample is measured using the system, the system should reproduce the known reflectance data. A third purpose of periodic calibration is to obtain information that will enable merging multiple raw exposure images into one spectral image. The first two purposes require having a spectral reflectance image of a standard reflectance sample surface, e.g., a white standard reflectance sample surface, at the spatial resolution of the imaging system 134.

Figure 7:
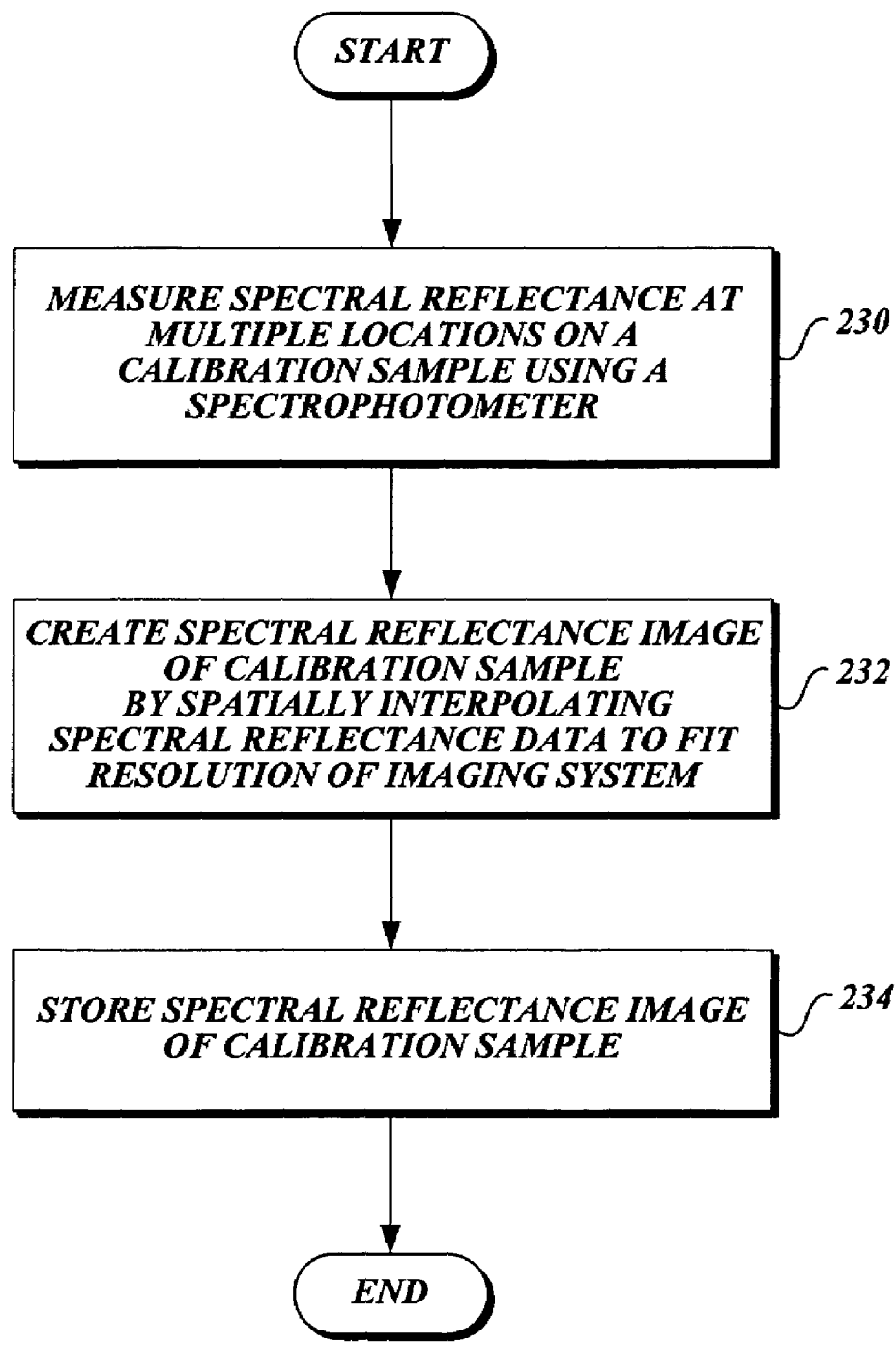
FIG. 7 is a flow diagram illustrating an exemplary calibration method suitable for characterizing a calibration surface.

An exemplary method for producing a spectral reflectance image of a white standard reflectance sample surface is illustrated in FIG. 7 and described below. Briefly described, the method starts at block 230 where the spectral reflectance at multiple locations on a calibration sample is measured using a spectrophotometer. At block 232, a spectral reflectance image of the calibration sample is created by spatially interpolating spectral reflectance data to fit the resolution of the imaging system 134. At block 234, the spectral reflectance image of the calibration sample is stored and the method ends. The actions described in blocks 230, 232, and 234 are taken because the calibration sample, i.e., the white standard reflectance sample surface, may have spatial variations that are large enough to be detected by the imaging system 134. For example, the calibration sample may be whiter in the upper left corner compared to the lower right corner. Such variations in the calibration sample are determined in FIG. 7 such that the variations in the calibration sample can be separated from variations in the LED illuminations. To determine the calibration variation, a standard spectrophotometer is used to measure the reflectance of the calibration sample at a number of spatial locations (block 230) and these measurements are interpolated (block 232) to create a spectral reflectance image of the calibration sample at the resolution of the imaging system 134. This method assumes that the spectral reflectance variations on the calibration sample occur at a much slower rate compared to the measured spatial sampling rate made by the standard spectrophotometer. Those skilled in the art will appreciate that this ensures that the Nyquist criteria is met and that the interpolation is a valid estimate of the calibration sample's true spectral reflectance variation.

The calibration sample's spectral reflectance image, which comprises an array of pixel values, produced by the calibration method illustrated in FIG. 7 and described above, is stored for use in an exemplary calibration calculation described below. In the exemplary calibration calculation, a pixel value in the calibration sample's spectral reflectance image is denoted as a vector $w_{ij}$ and provides the spectral reflectance of the calibration sample at spatial location i,j. The spectral reflectance at location i,j is represented by an N element vector in which each element is the spectral reflectance of the sample at a particular wavelength. For example, if $w_{ij}$=[x1, x2, . . . , xN] and N=31 and the region of interest of the electromagnetic spectrum is from 400 nm to 700 nm and the desired spectral resolution is 10 nm, then x1 represents the spectral reflectance at location i,j for wavelength 400 nm; x2 represents the spectral reflectance at location i,j for wavelength 410 nm, and so on up to x31 which represents the spectral reflectance at location i,j for wavelength 700 nm.

It should be noted that the exemplary method for producing a spectral reflectance image of a white standard reflectance sample surface illustrated in FIG. 7 and described above need not be performed each time the system is calibrated. Rather, preferably, the exemplary method for producing a spectral reflectance image of a white standard reflectance sample surface illustrated in FIG. 7 is performed once, e.g., when a spectrophotometric camera is assembled. The spectral reflectance image of the white standard reflectance sample surface produced using the method illustrated in FIG. 7 is stored in the microcomputer 136. The pixels of the pixel array comprising the spectral reflectance image are denoted by the vectors $w_{ij}$ and used in calculations presented later herein. Preferably, similar spectral reflectance images are produced and stored for a set of standard reflectance sample surfaces including a white sample and a plurality of neutral samples. An exemplary set of standard reflectance sample surfaces comprise a white sample, as described above with at least 90% nominal reflectance, and three neutral, i.e., gray, samples with nominal reflectances of 1%, 10% and 50%. The spectral reflectance images of the neutral samples are used to merge multiple exposures into one spectral reflectance image.

Figure 10:
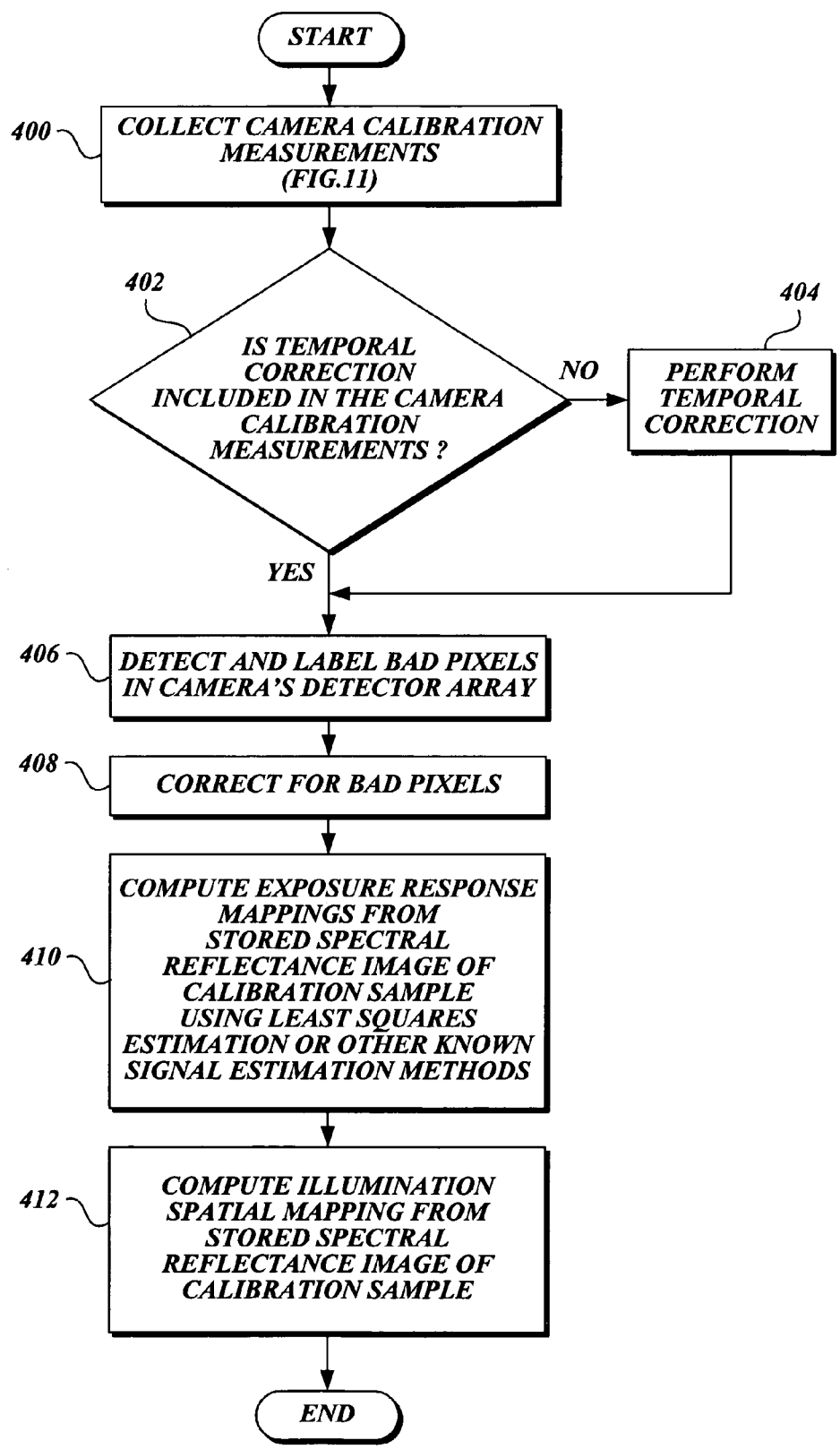
FIG. 10 is a flow diagram illustrating an exemplary method for calibrating an exemplary system used to create spectral reflectance images.

Returning to block 200 of FIG. 6, periodic calibration is performed using an exemplary periodic calibration method illustrated in FIG. 10 and described below. The method of FIG. 10 begins at block 400 where the calibration measurements are collected. In FIG. 10, at decision block 402, a test is made to determine if temporal correction is included in the camera calibration measurements. If temporal correction has been included, the control flows to block 406. If, at decision block 402, it is determined that no temporal correction has been included in the calibration measurements, the control flows to block 404 where temporal correction is performed. An exemplary temporal correction process using equation (5) is described below. Then, control flows to block 406. At block 406, bad pixels in the camera's detector array are detected and labeled. A bad pixel is a pixel element in a CCD array that does not respond to incident light. Bad pixels often appear as solid white or black. An exemplary way of detecting bad pixels is to capture an image of a known white and a known black sample and examine threshold values. For example, a white image is captured. Pixels that appear black in the image are bad pixels and labeled as such. At block 408, a correction is made for bad pixels. An exemplary way to correct for a bad pixel is to linearly interpolate the value of the bad pixel using the values of the bad pixel's neighboring pixels. At block 410, exposure response mappings are computed from stored spectral reflectance images of calibration samples (obtained in the manner described above in connection with FIG. 7) using least squares estimation or other known signal estimation methods. At block 412, illumination values are computed for the spatial mapping from the stored spectral reflectance images of the calibration sample and the method ends.

Figure 11:
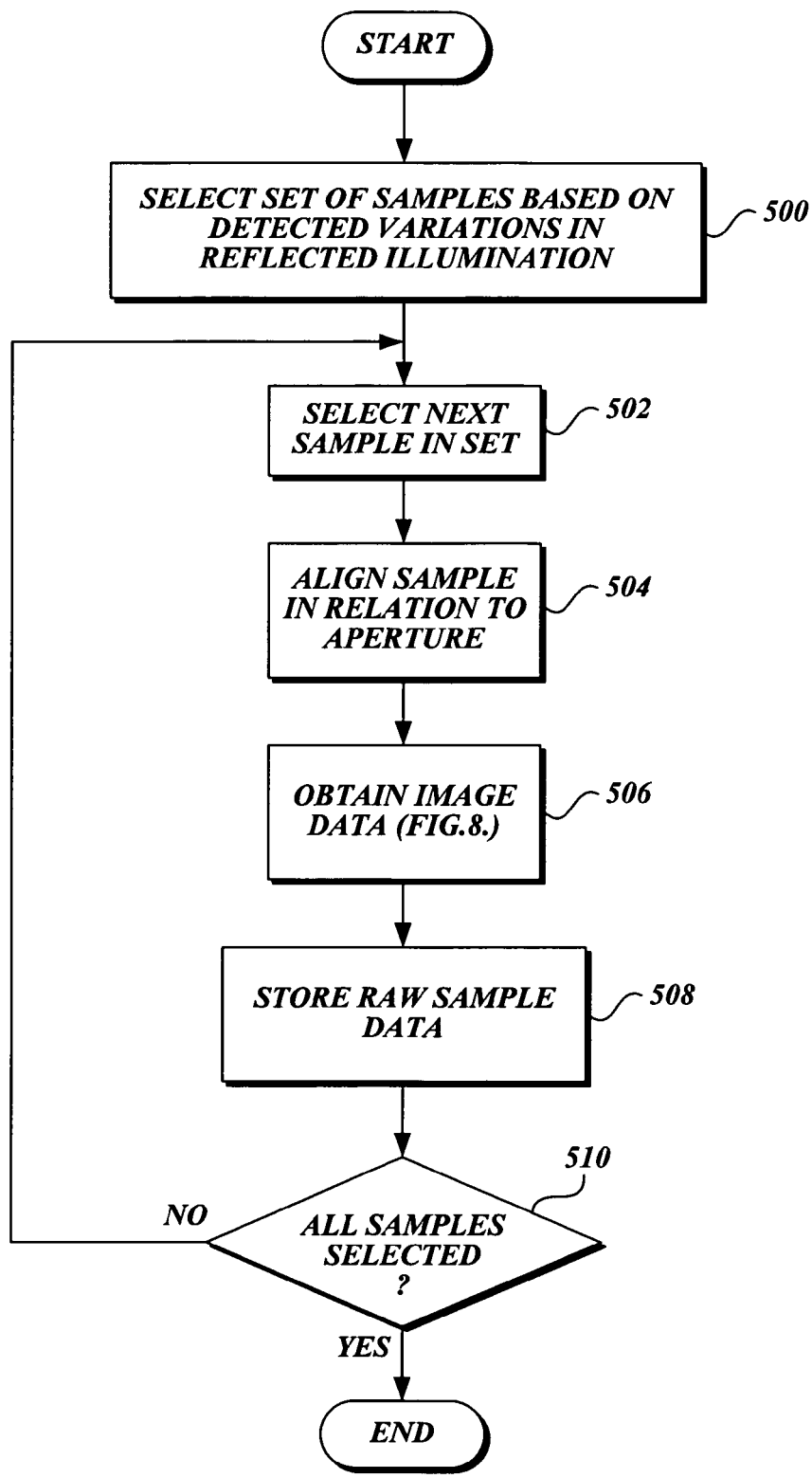
FIG. 11 is a flow diagram illustrating an exemplary method for collecting camera calibration measurements suitable for use in FIG. 10.

An exemplary method for collecting the system calibration measurements used in block 400 of FIG. 10 is illustrated by the flow diagram in FIG. 11. The exemplary method of FIG. 11 begins at block 500 where a set of samples is selected based on the detected variations in reflected illumination of each sample. As noted above, an exemplary set of samples comprise a white sample with a nominal reflectance around 90% and three neutral samples with nominal reflectances of 1%, 10% and 50%. At block 502, the next sample, e.g., first sample, in the set of sample surfaces is selected. At block 504, the selected sample surface is aligned in relation to the aperture. At block 506, image data is obtained using the method illustrated in FIG. 8 and described below. At block 508, the spectral reflectance (raw sample data) is stored. At decision block 510, a test is made to determine if all samples have been selected. If all samples have been selected, the method ends. If all samples have not been selected, the control flows back to block 502.

The data collected during the calibration method illustrated in FIG. 11 and described above is used to adjust the recorded data of the target surface 104. In addition to the above calibration measurements, additional information about the system is required to ensure accurate correction of the raw recorded data. In particular, a matrix S and a diagonal matrix $D_{ij}$ are determined. With N being the number of spectral power samples for a given LED and M being the number of LEDs, S is an N×M matrix whose columns are the spectral power distributions of M LEDs. $D_{ij}$ is an N×N diagonal matrix that represents the spectral sensitivity of the camera including the CCD array and optical components, e.g., lenses, IR filter etc. S is the relative spectral power distribution of the LEDs in the LED array 120 and is determined by spectroradiometric sampling. That is, a spectroradiometer is used to measure the spectral power distribution of each LED. A column of matrix S is one of these measurements. The diagonal matrix $D_{ij}$ is the relative spectral sensitivity of the multiple pixel sensor array 102 at the pixel location i,j whose value is determined by using a grating based monochromatic source generator and a spectroradiometer. The values for S, $D_{ij}$, and $w_{ij}$ are used in determining the corrections of blocks 410 and 412 in FIG. 10. The determination of the corrections to apply (blocks 410 and 412 FIG. 10) and the application of the corrections (blocks 216, 218 and 222, FIG. 6) to the recorded data from sample 104 are described below.

Returning to FIG. 6 at block 202, a sample is mounted in the exemplary spectrophotometric system illustrated in FIG. 2. The sample (not shown in FIG. 2) has a surface to be measured, i.e., the target surface 104. At block 204, M by E raw data images of the sample, i.e., the target surface 104, are obtained. As noted above, M represents the number of wavelength bands for which raw data images are obtained i.e. the number of LEDs. E represents the number of exposures, i.e., the number of raw data images, collected for a particular LED. The total number of raw data images is the product of M multiplied by E. It is preferable to produce more than one exposure, i.e., more than one raw data image, for each wavelength band and merge the plurality of exposures into one raw data image when spectrophotometric system embodiments with less sophisticated and/or less expensive imaging systems are used. An exemplary method for obtaining M by E raw data images is illustrated in the flow diagram shown in FIG. 8 and described next.

Figure 8:
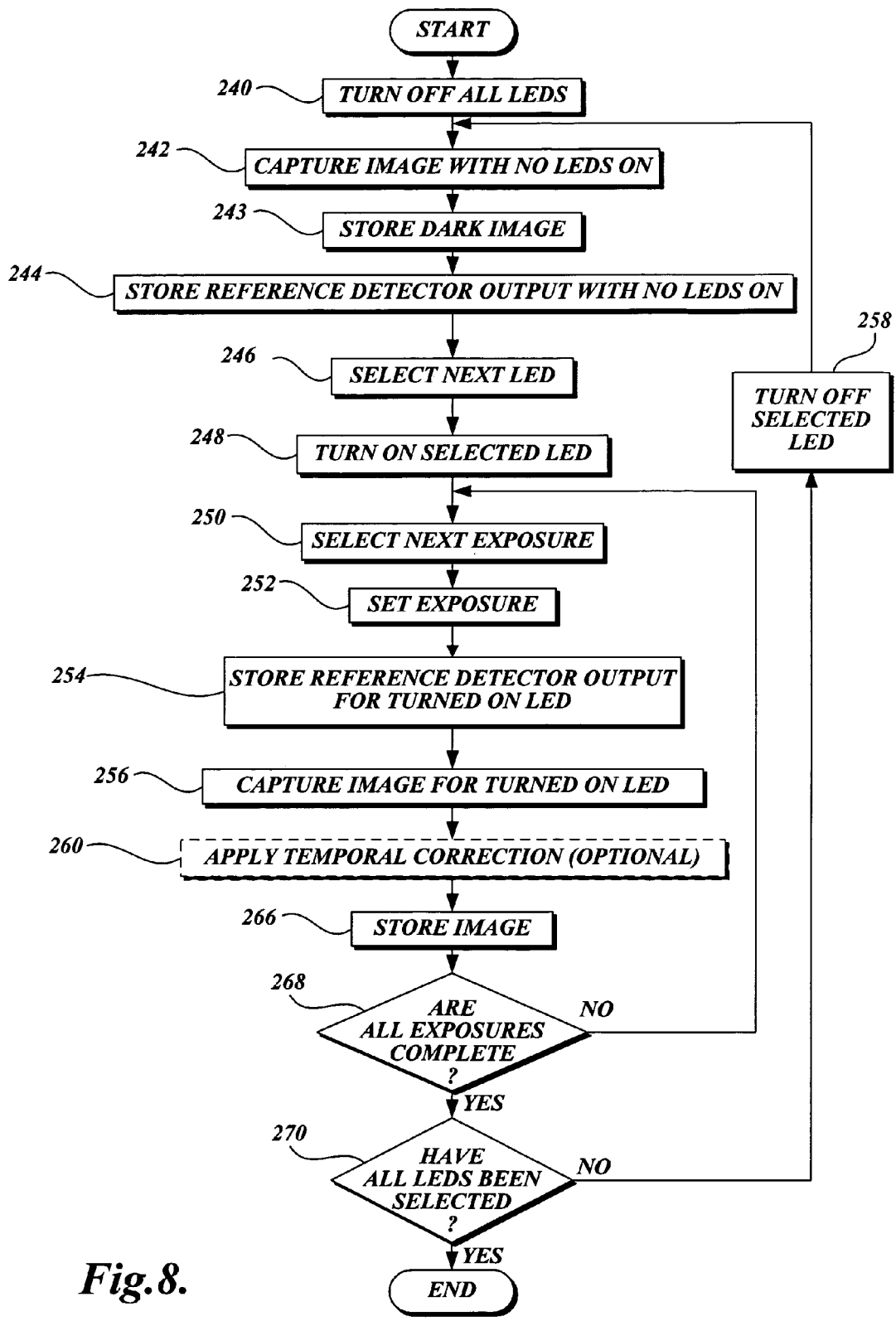
FIG. 8 is a flow diagram illustrating an exemplary sample measuring method suitable for use in FIG. 6.

The exemplary method illustrated in FIG. 8 starts at block 240 where all of the LEDs, i.e., all of the LEDS of the LED array 120, are turned off. Then, at block 242, an image, i.e., a spectral reflectance image, is captured by the imaging system 134 with no LEDs turned on. Next, at block 243 the captured dark image is stored. At block 244, the reference detector output with no LEDs turned on is stored, i.e., the analog input of the reference detector 106 is converted to digital form by the ADC 126 and the resulting digital data is stored. At block 246, the next, e.g., first, LED is selected. Next, at block 248, the selected LED is turned on.

At block 250, the next exposure, i.e., the next spectral reflectance image to be produced for the wavelength band produced by the turned on LED, is selected. For example, if it is determined that four exposures are required for each wavelength band, exposure 1 from a series of exposures 1, 2, 3, and 4 is selected. Next, at block 252, the exposure is set, i.e., preparations are made to produce the exposure. For example, data structures to store data for the exposure may be created by the measurement conversion software 140. Then, at block 254, the output of the reference detector 106 with the selected LED turned on is stored. That is, the portion of the light from the selected LED that is directed to the reference detector 106 and detected by the reference detector 106 produces a corresponding analog output signal. The analog output signal is converted into digital form by the ADC 126 and stored. At block 256, a spectral image, i.e., spectral reflectance image, is captured by the multiple pixel sensor array 102 for the wavelength band determined by the turned on (selected) LED.

At block 260, which is optional, temporal correction is applied. Depending on the implementation, it may be more desirable to apply temporal correction at block 210 (described below) of FIG. 6 rather than block 260 of FIG. 8. If temporal correction is applied at block 260, the corrected data is tagged so that temporal correction does not occur at block 210. How temporal correction is applied is described below in connection with block 210 of FIG. 6.

At decision block 268, a test is made to determine if all exposures have been completed for a particular wavelength band. If all exposures have not been completed, control flows back to block 250 where the next exposure is selected. If all exposures have been completed, control flows to decision block 270 where a test is made to determine if all LEDs have been selected, i.e., all LEDs in the LED array 120 have been sequentially cycled on. If all of the LEDs have been selected, the method ends. If all of the LEDs have not been selected, at block 258 the selected LED is turned off. Then, the control flows to block 242 where, once again, an image is captured with no LEDs turned on.

At the completion of FIG. 8, the system will have collected M times E raw spectral images as well as the measurements with the LEDs off and corresponding reference sensor measurements. In the exemplary method illustrated in FIG. 8 and described above, when each LED is turned on, a predetermined number (E) of raw data images, i.e., exposures, are produced. During each exposure, in addition to the raw data image being stored, data produced by the reference detector 106 is also stored. The exposures and the data produced by reference detector 106 are respectively modeled by equations (3) and (4), which are set forth below. In equation (3), $s_{ij}(q,t_k)$ is a vector in which each element contains exposure data for an LED for an exposure length q taken at time $t_k$ at spatial location i,j. For each LED, there are one or more exposures each taken at unique points in time.

$$s_{ij}(q,t_k) = G_{ij}(q,t_k)S^T D r_{ij} + b_{ij} \quad q = 1, \ldots, E \quad (3)$$

In equation (3), $G_{ij}(q,t_k)$ is an M×M diagonal matrix determined from the calibration measurements. In equation (3), $G_{ij}(q,t_k)$ models the illuminant spatial variation across the sample as well as spatial variation in the multiple pixel sensor array 102. $S^T$ is the transpose of S and hence, is an M×N matrix with rows that are the spectral power distributions for each LED. S is determined through measurements of the LEDs' output using a spectroradiometer. D is an N×N diagonal matrix representing the spectral sensitivity of the camera (i.e. optics and multiple pixel sensor array 102). $r_{ij}$ is the spectral reflectance of the sample surface 104 at location ij. Note that $r_{ij}$ is the desired quantity that the system will eventually provide as output. D is determined through direct measurement with a controlled monochromatic source generator. $b_{ij}$ is a vector of each pixel value measured when the LED is turned off. These values are the image pixel values measured in block 242 of FIG. 8. At this point in the calculation, the value of each parameter in equation (3) is known except $G_{ij}(q,t_k)$ and $r_{ij}$, which are calculated in the process described below.

The data produced by the reference detector 106 describe the temporal fluctuations of the LEDs during the exposures. This temporal variation in LED brightness must be removed from the data recorded by the multiple pixel sensor array 102. This removal process is referred to as temporal correction. The data produced by the reference detector 106 is recorded so that the data may be used in a temporal correction process described below. In equation (4), $f(t_k)$ is the data gathered from the reference detector 106 at time $t_k$. Preferably, the output of the reference detector 106 is recorded at the same time as the capture of the image by the multiple pixel sensor array 102.

$$f(t_k) = J(t_k) S^T D_r u + b_r \quad (4)$$

In equation (4), $J(t_k)$ is an M×M diagonal matrix whose elements account for the illumination brightness at time $t_k$. $D_r$ is an N×N diagonal matrix that represents the spectral sensitivity of the reference detector 106, u is a N-element vector whose elements all equal 1 and $b_r$ is a vector with M elements, one for each LED. The kth element of $b_r$ contains data collected from the reference detector when all the LEDs are turned off prior to making the measurement with the kth LED on.

Returning to FIG. 6 at decision block 208, a check is made to determine if temporal correction is included in the images, i.e., if temporal correction data is included in the raw data images at block 260 shown in FIG. 8. Temporal correction data is provided using data from the reference detector 106. The reference detector 106 provides time dependent data, i.e., temporal data, that indicates how the intensity of the light from a light source, e.g., an LED, changes or varies over time. Including temporal data in an image provides temporal correction. If temporal correction has been included in the images, the control flows to decision block 214. If temporal correction has not been included in the images, the control flows to block 210. In block 210, temporal fluctuations in LED brightness are removed by computing the ratio of the measurement collected by the multiple sensor array 102, which is modeled in equation (3), to the measurement from the reference detector 106, which is modeled in equation (4). The ratio is given by:

$$n_{ij}(q) = \frac{s_{ij}(q, t_k) - b_{ij}}{f(t_k) - b_r} \quad q = 1, \ldots, E \quad (5)$$

Note that equation (5) removes any temporal variations from LED brightness changes. For example, if an LED is twice as bright at time $t_k$ compared to time $2^*t_k$, then the measurement at time $t_k$ will be twice as large for $s_{ij}(q,t_k)$ (the measurement with the multiple pixel sensor array 102) and for $f(t_k)$ (the measurement with the reference detector 106) at time $t_k$ compared to time $2^*t_k$. Dividing the quantities $s_{ij}(q,t_k)$ and $f(t_k)$ after the removal of any signal bias (the terms $b_{ij}$ and $b_r$) will remove the temporal fluctuations and $n_{ij}(q)$ will be independent of $t_k$.

The remaining steps require the use of the calibration data that was collected in block 200 (FIG. 6) using the exemplary method illustrated in FIG. 10. The measurement of each calibration sample had temporal correction applied to the measurements (blocks 402 and 404, FIG. 10). For example, temporal correction for the white reflectance surface is expressed similar to equation (5) and is given by:

$$n_{ij}(W) = \frac{w_{ij}(t_w) - b_{ij}}{f(t_w) - b_r} \quad (6)$$

In equation (6), $t_w$ represents the time at which the spectral data was gathered for the white reference surface. The temporal correction is applied to each calibration tile measurement (blocks 402 and 404, FIG. 10).

Continuing with the method illustrated in FIG. 6, at decision block 214, a test is made to determine if there are multiple exposures for each wavelength band. The integration time of the imaging system 134, i.e., the exposure time q, is preferably optimized to ensure that the spatial variation of the reflected illumination is detectable across the target surface 104. In physical terms, optimization occurs when an LED of the LED array 120 is turned on long enough to allow enough spectral energy to strike the target surface 104 and be reflected long enough for the multiple pixel sensor array 102 to receive enough spectral energy to detect variations in the spectral energy reflected from the target surface 104. Measuring sample variation that is greater than the linear dynamic range of the sensors in the multiple pixel sensor array 102 is compensated for by capturing multiple spectral images, i.e., exposures, and combining the data from the multiple exposures into one spectral image.

At block 216 of FIG. 6, exposure images for each band are merged using equation (7) and the calibration data collected in block 200 of FIG. 6. The determination of the mapping is in block 410 (FIG. 10). Each calibration tile is recorded with a specific exposure time for each LED. If the spectral reflectances of the set of tiles have average reflectance across the imaged region of 1%, 10%, 50%, and 90%, then the 1% tile will receive the longest exposures while the 90% tile will receive the shortest exposures. The chosen exposure time is designed to maximize the dynamic range of the imaging system for that particular tile. For example, consider LED m and calibration tile n. The multiple pixel sensor array of 102 FIG. 1 is exposed a time $t_{mn}$ such that the average pixel value in the recorded image when illuminating calibration tile n with LED m is ½ the bit range of the imaging system. For example, this value would be 128 for an 8-bit imaging system.

The merging of multiple exposure images from an unknown sample surface 104 (FIG. 1) is performed using the knowledge of the exposure times required for the calibration samples of known average reflectance. As an exemplary method, suppose the imaging system 134 (FIG. 2) has eight bits of resolution and suppose there were four exposure images collected for LED m on the target surface 104. In addition, let the exposure time for exposure k be the time required for the kth calibration tile to reach an average pixel value of 128. Finally let the average reflectance on the kth calibration tile to be given by $p_k$ with $p_1<p_2<p_3<p_4$. Denote the pixel value at spatial location i,j that is created by the four exposures of target surface 104 (FIG. 1) with LED m as $n_{ij}(1)$, $n_{ij}(2)$ $n_{ij}(3)$ and $n_{ij}(4)$ for exposure 1, 2, 3 and 4. Now consider the nonlinear functions F, G, and H given by $$F(a) = \begin{cases} 1 & X \leq a \\ 0 & \text{else} \end{cases}$$

$$G(a) = \begin{cases} 1 & X \leq a \leq Y \\ 0 & \text{else} \end{cases}$$

$$H(a) = \begin{cases} 1 & a \leq Y \\ 0 & \text{else} \end{cases}$$

With the above definitions, a merging of the four exposures can be expressed as $$n_{ij} = \frac{\frac{p_1}{p_4}n_{ij}(1)H(n_{ij}(1)) + \frac{p_2}{p_4}n_{ij}(2)G(n_{ij}(2)) + \frac{p_3}{p_4}n_{ij}(3)G(n_{ij}(3)) + n_{ij}(4)F(n_{ij}(4))}{H(n_{ij}(1)) + G(n_{ij}(2)) + G(n_{ij}(3)) + F(n_{ij}(4))} \quad (7)$$

Those skilled in the art will understand that this process normalizes the multiple exposures to a common scale and averages them into a single image. Those skilled in the art will also understand that the number of exposures needed depends upon the dynamic range and the linearity of the image system 134 as well as the desired dynamic range of the merged pixels in the image. The threshold constant values X and Y above should be selected to ensure that only measurements that are within the linear operating region of the image system 134 are used in the construction of $n_{ij}$.

This merging of multiple exposure images, occurs for each LED. That is, an appropriate version of equation (7) is applied to each element of $n_{ij}(q)$ across the exposure values q=1, ... E, which reduces these exposure images for each LED to a single image. A pixel element in this image at location i, j is denoted by $n_{ij}$. The image comprises M bands (one for each LED). Hence, $n_{ij}$ is an M element vector whose kth element represents the reflectance of the sample relative to the kth LED.

Continuing with block 218 of FIG. 6, the variations in the image due to nonuniform light distribution and to sensor uncertainty of the absolute value of the measurement are removed using equations (8) through (11). For example, if a location i,j is more brightly illuminated by an LED compared to another location, then this variation must be removed to recover the true spectral reflectance (i.e. $r_{ij}$ of equation (3)) of the sample surface 104. The removal of the temporal variation in equation (5) and the merging of the multiple exposure images in equation (7) enables us to model the pixel element given by $n_{ij}$ using equation (8).

$$n_{ij}=G_{ij}S^TDr_{ij} \quad (8)$$

In equation (8), $n_{ij}$ is pixel i,j of the combined multiple exposure image. $G_{ij}$ is a M×M diagonal matrix that is calculated using equation (11), and models the spatial variation of the LEDs in LED array 120 and the spatial variation of the spectral sensitivity of the multiple pixel sensor array 102. $S^T$ is the relative spectral power distribution of the LEDs in LED array 120 that is determined by spectroradiometric measurement. D is the relative spectral sensitivity of the multiple pixel sensor array 102 determined by using a grating based monochromatic source generator and a spectroradiometer. The term $G_{ij}$ contains all the spatial variations introduced by nonuniformity of the illumination onto the sample 104 as well as any spatial variation that exists in the spectral sensitivity of the multiple pixel sensor array 102. For example, for the same incident illumination, the pixel in the array at location i, j may report a higher value compared to a pixel at another location. Through compensation of the variation, a more accurate spectral reflectance of sample surface 104 denoted by $r_{ij}$ in equation (8) can be obtained.

Determining $G_{ij}$ requires the use of the white calibration sample that was measured in FIG. 7. The same tile was also measured during the calibration process block 200 FIG. 6. Using the same model as is given in equation (8), the measurement of the white calibration sample in block 200 FIG. 6 can be expressed as equation (9).

$$n_{ij}(W)=G_{ij}S^TDw_{ij} \quad (9)$$

In equation (9), each of the parameters have known values except the M×M diagonal matrix $G_{ij}$. Recall that $S^T$ is the relative spectral power distribution of the LEDs in LED array 120 that is determined by spectroradiometric measurement. D is the relative spectral sensitivity of the multiple pixel sensor array 102 determined by using a grating based monochromatic source generator and a spectroradiometer. The white sample spectral reflectance variation denoted by the N element vector $w_{ij}$ was determined using the method describe above and in FIG. 7. For the pixel location i,j the M×M diagonal matrix $G_{ij}$ can be determined first by computing the vector $v_{ij}$ where $$v_{ij} = S^T D w_{ij} \qquad (10)$$

at which point $G_{ij}$ is solved by equation (11):

$$G_{ij} = \text{Diagonal}\left[\frac{n_{ij}(W)}{v_{ij}}\right] \qquad (11)$$

In solving for $G_{ij}$, the above division is performed element by element. Again, it should be noted that this requires knowing the spatial variation of the white calibration reference surface, which is represented by $w_{ij}$. The spatial variation of the white reference surface is obtained by measuring the white reference surface—at a number of spatial points with a standard reflectance spectrophotometer using a spatial sampling rate sufficient to allow interpolation of the white reference surface spectral reflectance to the resolution of the imaging system 134. This approach requires that the calibration spectral reflectance varies spatially at a rate that is less than half the sampling rate used with the standard reflectance spectrophotometer. In this case, the variations in the image due to the nonuniformity of light distribution and the uncertainty of the absolute value of the measurement are removed.

At block 220, an action is taken, e.g., interpolation, to correct for pixels labeled as bad. The bad pixels for which correction is applied are the same bad pixels detected and labeled in block 406 of FIG. 10 during the calibration method described above.

At block 222, the vector that contains elements that determine the spectral reflectance at each location (i.e. $r_{ij}$) is applied to the $n_{ij}$ values using equation (12). More specifically, the goal of the method illustrated in FIG. 6 and the purpose of the last block (block 222) is to determine $r_{ij}$, a vector that contains elements that specify the spectral reflectance at each of the locations specified by i and j. Providing the spectral reflectance at each of the spatial locations specified by i and j produces a spectral image that is spectrally corrected, yielding the results of the method shown in FIG. 6. This last step in the processing, which yields a spectrally corrected spectral image, is performed using equation (12).

$$\hat{r}_{ij} = K_r H_{ij}(H_{ij}^T K_r H_{ij} H + I\sigma)^{-1} n_{ij} \qquad (12)$$

In equation (12), $I\sigma$ provides regularization to the matrix inversion and $H_{ij} = G_{ij} S^T D$. The N×N matrix $K_r$ is the estimated autocorrelation matrix for an ensemble of typical reflectance spectra that the device may be used to measure. The $n_{ij}$ value is the pixel value at location row i, column j in a matrix representing a spectral image after correcting for the temporal variations in the spectral image and combining the multiple exposures into one spectral image. If there are M unique types of LEDs used in the spectrophotometric camera, then the pixel value $n_{ij}$ is an M element vector. For example, a standard RGB image has a 3 element vector at each pixel location, hence for an RGB image M equals 3. The mapping in equation (12) is a linear mapping from an M element vector to a N element vector where N is the number of samples representing the visible spectrum. As described above, with the appropriate spectral energy sources, e.g., LEDs, samples for the IR and UV regions of the electromagnetic spectrum could also be represented. Note that equation (12) reduces to a N×M matrix, i.e., $r_{ij} = X_{ij} n_{ij}$ where $X_{ij}$ is an N×M matrix, and that each pixel location with i and j indices has its own matrix due to the dependency of $H_{ij}$ on the location indices i and j. This dependency is used to adjust for the illumination spatial variation in equation (12) (via the computed value of $G_{ij}$ in equation (11)). For example, a location ij with more illumination from a green LED will have a different $X_{ij}$ compared to a location with less illumination from the same green LED. It should be noted that equation (12) is a linear minimum least square error estimator. Those skilled in the art will appreciate that other types of estimators may be applied. After block 222, the method illustrated in FIG. 6 ends.

Figure 9A:
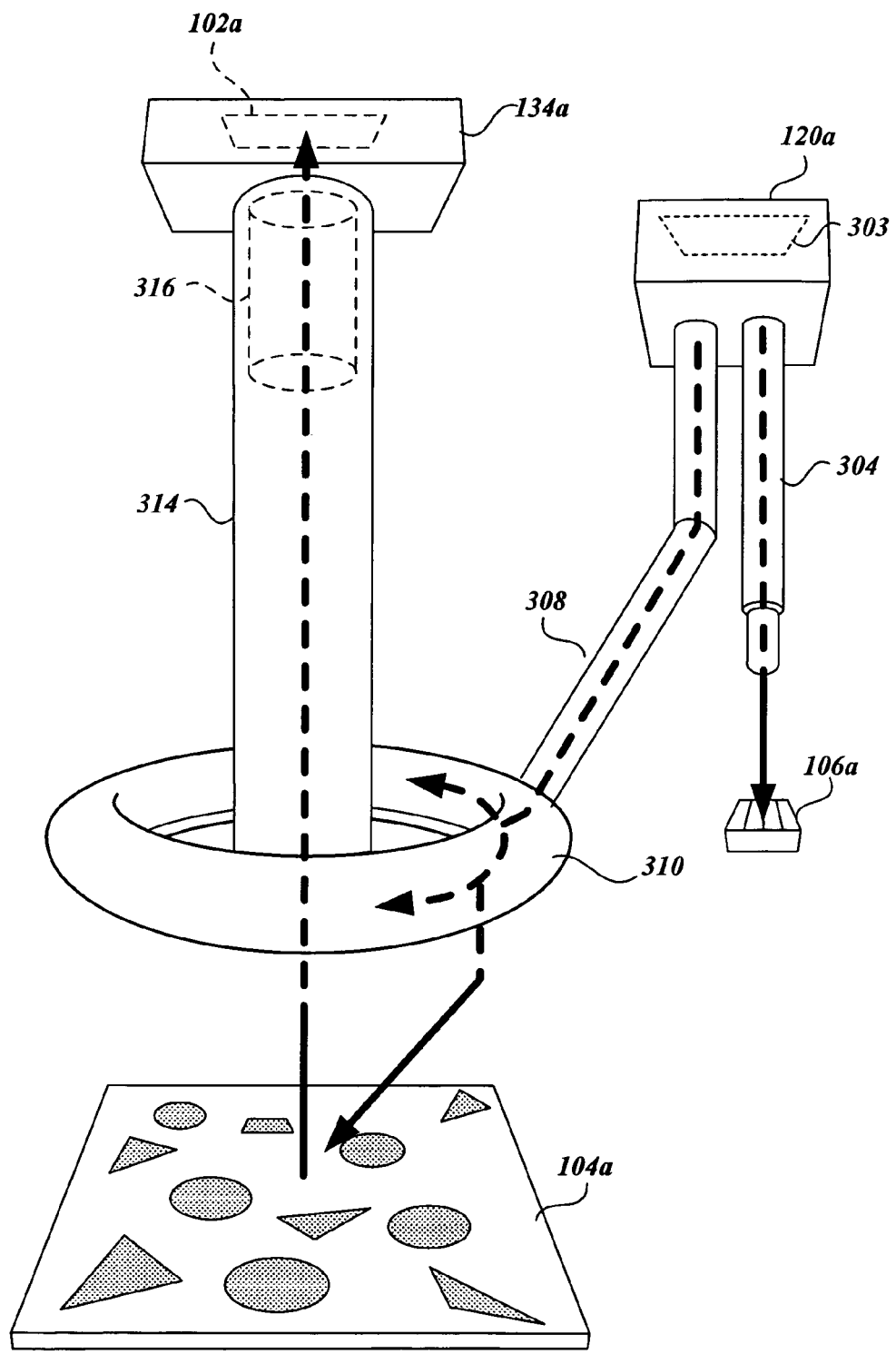
FIG. 9A is a pictorial illustration of an exemplary system that provides spectral reflectance data for a plurality of locations on a surface.

As will be readily appreciated by those skilled in the art, an exemplary spectrophotometric system is illustrated in FIGS. 1-5, suitable for employing the methods illustrated by the exemplary flow diagrams shown in FIGS. 6-8, 10 and 11 and described above. The exemplary spectrophotometric system can be optically implemented in various ways to measure the spectral reflectance for a plurality of wavelength bands at a plurality of locations on a surface. An exemplary optical implementation is illustrated in FIG. 9A. The exemplary optical implementation illustrated in FIG. 9A includes a light source 120a containing the LED array 303 that provides a spectral energy source for sequentially producing spectral energy in different wavelength bands, as described above. More specifically, a selected LED of the LED array 303 is turned on producing light in a particular wavelength band while all of the other LEDs are turned off. The light from the turned on LED of the LED array 303 is directed by a first light pipe 304, i.e., a spectral energy pipe, to the reference detector 106a. A light or spectral energy pipe is a device capable of conducting or directing light, with negligible light loss, from one location, e.g., the light source 303, to another location, e.g., the reference detector 106a. Exemplary light pipes are optical fibers, fiber optic cables, fiber optic cable bundles, etc. Light pipes may be made of glass, acrylic or other suitable materials. The light from the first light pipe 304 is directed to the reference detector 106a.

The light from the selected LED of the LED array 120a is also directed by a second light pipe 308 to a light pipe ring 310. A light pipe ring is a light pipe that has been formed into a ring shape. The light pipe ring 310, like a light pipe, conducts or directs light. In the case of FIG. 9A, the light received from the second light pipe 308 is conducted or directed by the light pipe ring 310 to the target surface 104a in an omnidirectional manner, e.g., through a 360 degree arc. Providing omnidirectional light results in the target surface 104a receiving more intense and consistent light than is possible with light received from a single direction.

Figure 9B:
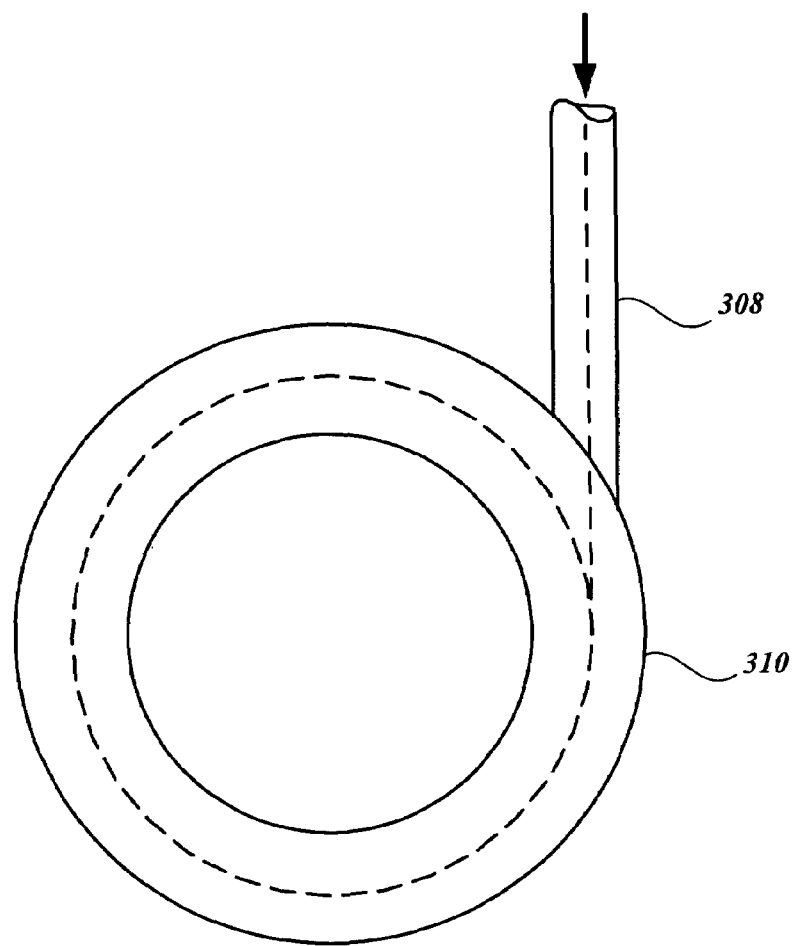
FIGS. 9B-9C are pictorial illustrations of an exemplary light pipe ring suitable for use in FIG. 9A.
Figure 9C:
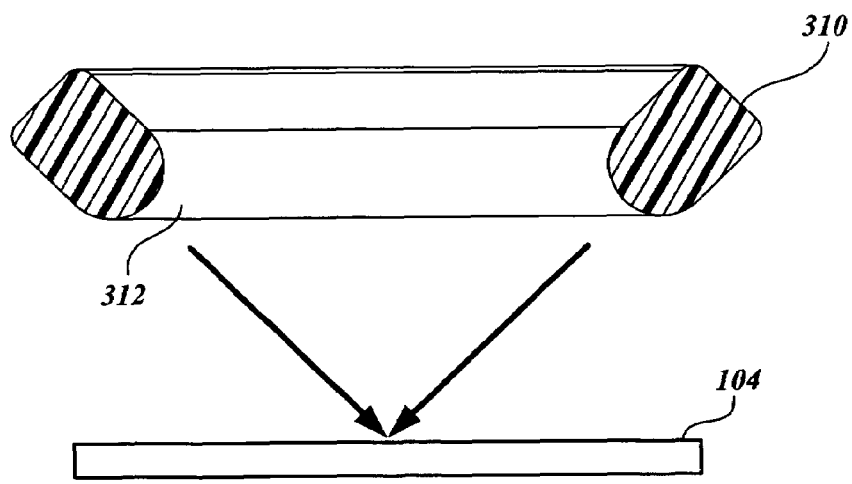

FIGS. 9B and 9C illustrate an example of a light pipe ring 310 suitable for directing omnidirectional light onto the target surface 104 at a 45 degree angle. More specifically, in a straight light pipe, light is internally reflected along the length of the light pipe. When a light pipe is bent, light is internally reflected along the length of the bent light pipe as long as the radius of the bend is such that the tangent angle at all points along the surface of the light pipe remain below a critical angle, i.e., the angle at which the light is no longer internally reflected and exits the light pipe. It is possible to size a light pipe ring such that light enters the ring and continues to be internally reflected. FIG. 9B illustrates such a light pipe 310. Light entering the light pipe 310 from the second light pipe 308 is internally reflected throughout the light pipe ring 310. Rather than being round in cross-section, as shown in FIG. 9C, the light pipe ring 310 has a "U" cross-sectional shape. The bottom of the U shape is a curved section 312 that runs along the inner circumference of the light pipe ring 310. The curved section 312 forms an angle that is greater than the critical angle, i.e., the angle at which the light exits the light pipe ring 310. Hence, the curved section 312 functions as a lens that directs light out of the light pipe ring 310. The positioning of the curved section 312 is such that the exiting light strikes the target surface 104 at a 45 degree angle. The sizing of the light pipe ring and the positioning of the light pipe ring with respect to the target surface 104 is such that the light hits an appropriate sized spot on the target surface. It is possible to direct light from a plurality of directions onto a surface at a prescribed angle using devices other than light pipe ring 310. Hence, using a light pipe ring, such as light pipe ring 310, to omnidirectionally direct light onto the target surface 104 should be construed as exemplary and not limiting.

Returning to FIG. 9A, the light reflected from the target surface 104a is received by a cylindrical enclosure 314 positioned orthogonal to the target surface 104a and co-axially aligned with the light pipe ring 310. The cylindrical enclosure prevents unwanted light, i.e., light other than the light reflected from the target surface 104a, from entering a blocking aperture 316 located at the exit end of the cylindrical enclosure 316. The blocking aperture 316 further prevents unwanted light from entering the imaging system 134a, which contains the sensor array 102a. As previously described, the imaging system 134a is controlled by a microcontroller, such as microcontroller 130, and a microcomputer, such as microcomputer 136. The imaging system 134a can take the form of a suitably controllable digital camera or a specifically designed imaging system including a focusing lens (not shown) and a suitable aperture 316.

Spectral images produced by an optical system, such as the optical system illustrated in FIGS. 9A-C and described above, processed by a method for processing spectral images, such as the method illustrated by FIGS. 6, 7, 8, 10, and 11 and described above, may be viewed on the display of a computing device or may be printed and viewed as a hardcopy image. As described above, a spectral image produced by a spectrophotometric camera viewed on a display may be manipulated to enable the selection of a region of interest (ROI). Once selected, the ROI may be enlarged for easier viewing or various operations may be applied to the ROI. Operations include, but are not limited to, obtaining the average spectral reflectance of an ROI and separating various spectral components of an ROI. Exemplary operations include, but are not limited to, analyzing and segmenting the spectral reflectance images; computing errors in the spectral reflectance images; computing statistics from the spectral reflectance images; and extracting features from the statistics. A spectral image may also provide input data for computer controlled devices used in automated processes. For example, a spectral image produced by a spectrometric system may be input into a computer controlled system for textile production to control dye or print quality, a computer controlled system for printing to provide feedback on print quality, or as a tool for watermark detection or to detect counterfeit currency.

Features may be added to record additional aspects of surface appearance such as, but not limited to, fluorescence and gloss. For example, in an embodiment, the fluorescence of the target surface 104 may be detected by adding a lens and a third light director that collects reflected spectral energy from the target surface 104 and directs the reflected spectral energy to a spectroradiometer. The spectroradiometer analyzes the spectral content of the reflected spectral energy. If the spectroradiometer detects spectral energy outside the energy band, i.e., wavelength band, of a turned on LED, the presence of fluorescence from the target surface 104 may be inferred. The third light director is placed near the multiple pixel sensor array 102 at an angle that as close to zero degrees as possible without disturbing or occluding the multiple pixel sensor array 102.

In another exemplary embodiment, the gloss of the target surface 104 may be detected by adding a third light director that directs a portion of the light from light source 100 to the target surface 104 at an angle of 60 degrees from perpendicular and from one direction. A fourth light director is placed opposite the third director that collects reflected spectral energy at an angle of 60 degrees from perpendicular and opposite the direction of the third light director. The reflected spectral energy is directed by the fourth director to a second reference detector similar to the reference detector 106. The ratio of measurements from the second reference detector to the measurements from the multiple pixel sensor array 102 are compared to measurements of sample surfaces with known levels of gloss.

In yet another exemplary embodiment, the light source 100, comprising a serially selectable plurality of LEDs, may be replaced by a single light source and color filter wheel. The light from a single bright light source, preferably a xenon lamp, radiates through a motor driven mechanical wheel containing a plurality of color filters, i.e., a color filter wheel. Instead of turning a particular LED on and turning off the remaining LEDs, the color filter wheel is rotated to position a color filter in the plurality of color filters such that the light from the single bright light source radiates through only the positioned color filter thus providing light of a particular wavelength band. A color filter wheel may filter the light directed to the sample surface 104 and not to the reference detector 106 or may filter both the light directed to the sample surface 104 and directed to the reference detector 106.

In an exemplary embodiment in which the spectral power distribution of the light from the light source 100 significantly changes over time, the reference detector 106 may need to be a spectroradiometer. A spectroradiometer enables measuring changes in the spectral power distribution. The measured changes may be placed into matrix S and used to adjust for the differences in spectral power distribution. Preferably, the spectral power distribution of the light from the light source 100 does not significantly change over time permitting the reference detector 106 to be a photodetector, a simpler and less expensive detector than a spectroradiometer.

While illustrative embodiments have been illustrated and described, it will be appreciated that various changes can be made therein without departing from the spirit and scope of the invention. For example, in an embodiment, the exemplary method illustrated in FIG. 8 may be modified such that the actions performed in blocks 242, 243 and 244 are performed in parallel with the action in block 256. As described above, at block 242, a spectral reflectance image is captured with no LEDs turned on; at block 243 the captured dark image is stored; at block 244, the reference detector output with no LEDs turned on is stored; and at block 256, a spectral reflectance image, is captured by the multiple pixel sensor array 102 for the wavelength band determined by the turned on LED. Actions performed in blocks 242, 243, 244, and 256 may be performed in parallel by using a second reference sensor and a plurality of occluded elements in the multiple pixel sensor array 102. The occluded elements in multiple pixel sensor array 102 receive no light and thus provide a dark measurement even when an LED is on. The second reference sensor and occluded elements in multiple pixel sensor array 102 provide a thermal drift measurement for thermal drift occurring during the actions in blocks 242 243 and 244. An advantage of such an embodiment is that the thermal drift measurement occurs while the LED that is on is measured thus providing a faster overall measurement cycle.

The embodiments of the invention in which an exclusive property or privilege is claimed are defined as follows:

1. A spectrophotometric system comprising:
    (a) a spectral energy source for sequentially producing spectral energy in different wavelength bands;
    (b) an imaging device including an array of sensors for detecting spectral energy;
    (c) a first spectral energy director for directing spectral energy produced by said spectral energy source onto a target surface;
    (d) a second spectral energy director for directing spectral energy reflected from the target surface to the array of sensors;
    (e) a reference detector for detecting changes in the spectral energy of each wavelength band produced by the spectral energy source;
    (f) a memory storing a set of calibration data representing irregularities in the spectral energy as detected by the array of sensors; and
    (g) an adjusting device coupled to the array of sensors, the reference detector, and the memory for adjusting the spectral energy detected by the array of sensors based on the changes in illumination detected by the reference detector and irregularities in the spectral energy as detected by the array of sensors represented by the set of calibration data stored in the memory.

2. The spectrophotometric system of claim 1, wherein different wavelength bands are selected from the visible band of the electromagnetic spectrum.

3. The spectrophotometric system of claim 1, wherein the different wavelength bands are selected from the ultraviolet band of the electromagnetic spectrum.

4. The spectrophotometric system of claim 1, wherein the different wavelength bands are selected from the infrared band of the electromagnetic spectrum.

5. The spectrophotometric system of claim 1, wherein the imaging device also includes focusing optics and an aperture.

6. The spectrophotometric system of claim 5, wherein the imaging device is a digital camera.

7. The spectrophotometric system of claim 6, wherein the digital camera is a monochromatic digital camera.

8. The spectrophotometric system of claim 1, wherein the first spectral energy director includes a light pipe.

9. The spectrophotometric system of claim 8, wherein the light pipe includes a ring.

10. The spectrophotometric system of claim 9, wherein the ring directs spectral energy onto the target surface omnidirectionally.

11. The spectrophotometric system of claim 10, wherein the spectral energy is directed onto the target surface at a 45 degree angle to the plane of the target surface.

12. The spectrophotometric system of claim 1 wherein the first spectral energy director directs light onto the target surface at a 45 degree angle to the plane of the target surface.

13. The spectrophotometric system of claim 1, wherein the second spectral energy director is a light pipe.

14. The spectrophotometric system of claim 13, wherein the light pipe receives spectral energy reflected from the target surface at an angle of 90 degrees to the plane of the target surface.

15. The spectrophotometric system of claim 1, wherein the spectral energy source is an array of light emitting diodes ("LEDs").

16. The spectrophotometric system of claim 15, wherein the LEDs produce spectral energy in different wavelength bands.

17. The spectrophotometric system of claim 16, wherein the adjusting device is furthermore coupled to the array of LEDs for selectively turning on and off the LEDs.

18. The spectrophotometric system of claim 17, wherein the LEDs are selectively turned on and off such that only one LED is turned on at a time and all other LEDs are turned off.

19. The spectrophotometric system of claim 1, wherein the array of sensors is formed by charge coupled devices ("CCDs").

20. The spectrophotometric system of claim 1, wherein the reference detector is a photodetector.

21. The spectrophotometric system of claim 1, wherein the reference detector is a spectroradiometer.

22. A method for collecting spectral reflectance data from a plurality of locations on a surface, comprising:
    sequentially directing spectral energy in different wavelength bands onto a target surface;
    collecting the spectral energy reflected from the target surface in an image formed of a plurality of pixels;
    detecting irregularities in the collected spectral energy across the plurality of pixels;
    detecting changes in the spectral energy in the different wavelength bands directed onto the target surface; and
    adjusting the image formed by a plurality of pixels based on the detected changes in the spectral energy and the detected irregularities in the collected spectral energy.

23. The method of collecting spectral reflectance data from a plurality of locations on a target surface of claim 22, wherein collecting the spectral energy reflected from the target surface in an image formed of a plurality of pixels comprises:
    obtaining the energy reflected from the target surface in a plurality of exposures formed of a plurality of pixels for a particular wavelength band; and
    combining the plurality of exposures to create an image formed of a plurality of pixels.

24. The method of collecting spectral reflectance data from a plurality of locations on a target surface of claim 22, wherein the spectral energy reflected from the target surface is collected in a separate image formed of a plurality of pixels for each different wavelength band.

25. The method of collecting spectral reflectance data from a plurality of locations on a target surface of claim 22, wherein the spectral energy in different wavelength bands is produced by an array of light emitting sources.

26. The method of collecting spectral reflectance data from a plurality of locations on a target surface of claim 25, wherein each light emitting source of the array of light emitting sources produces light in a different wavelength band.

27. The method of collecting spectral reflectance data from a plurality of locations on a target surface of claim 26, including selectively controlling the array of light emitting sources such that when one light emitting source is emitting light all other light emitting sources are not emitting light.

28. The system of claim 1 wherein the irregularities in the spectral energy as detected by the array of sensors comprise nonuniform light distribution and sensor uncertainty of the absolute value of the measurement.

29. The system of claim 1, wherein the spectral energy is adjusted further by interpolating to correct for pixels labeled as bad.

30. The method of claim 22, wherein the irregularities in the collected spectral energy across the plurality of pixels comprise nonuniform light distribution and sensor uncertainty of the absolute value of the measurement.

31. The system of claim 22, the image formed by the plurality of pixels is adjusted further by interpolating to correct for pixels labeled as bad.

32. The system of claim 1, wherein each sensor in the array of sensors is located at a pixel spatial location and each sensor measures a pixel; and wherein adjusting the spectral energy detected by the array of sensors comprises, for each wavelength band:
  adjusting for changes in illumination detected by the reference detector, by:
    determining a difference by subtracting from each measured pixel a measurement taken by the corresponding sensor when no spectral energy source is active; and
    dividing the difference by a change in illumination detected by the reference detector, and
  adjusting for irregularities in the spectral energy as detected by the array of sensors by:
    multiplying each measured pixel by a factor stored in the set of calibration data, the factor corresponding to the pixel spatial location of the measured pixel.

33. The system of claim 32, wherein the factor corresponding to the pixel spatial location of the measured pixel is the ratio of a true spectral reflectance of a calibration tile at that pixel spatial location over a measurement of the calibration tile by the sensor located at that pixel spatial location.

34. The method of claim 22, wherein the image formed by a plurality of pixels is adjusted by, for each wavelength band:
  adjusting for detected changes in the spectral energy by:
    determining a difference by subtracting from each measured pixel a measurement taken by the corresponding sensor when no spectral energy source is active; and
    dividing the difference by a change in illumination detected by the reference detector, and
  adjusting for detected irregularities in the collected spectral energy by:
    multiplying each measured pixel by a factor stored in the set of calibration data, the factor corresponding to the pixel spatial location of the measured pixel.

35. The method of claim 34, wherein the factor corresponding to the pixel spatial location of the measured pixel is the ratio of a true spectral reflectance of a calibration tile at that pixel spatial location over a measurement of the calibration tile by the sensor located at that pixel spatial location.

* * * * *